US009549781B2

(12) United States Patent
He et al.

(10) Patent No.: US 9,549,781 B2
(45) Date of Patent: Jan. 24, 2017

(54) MULTI-FORCE SENSING SURGICAL INSTRUMENT AND METHOD OF USE FOR ROBOTIC SURGICAL SYSTEMS

(71) Applicant: The Johns Hopkins University, Baltimore, MD (US)

(72) Inventors: Xingchi He, Columbia, MD (US); Iulian Iordachita, Lutherville-Timonium, MD (US); Marcin Balicki, Baltimore, MD (US); Russell H. Taylor, Severna Park, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 239 days.

(21) Appl. No.: 14/292,361

(22) Filed: May 30, 2014

(65) Prior Publication Data

US 2015/0342695 A1    Dec. 3, 2015

(51) Int. Cl.
*A61B 19/00* (2006.01)
*A61B 17/00* (2006.01)
(Continued)

(52) U.S. Cl.
CPC ......... *A61B 19/46* (2013.01); *A61B 17/00234* (2013.01); *A61B 34/10* (2016.02); *A61B 34/30* (2016.02); *A61B 90/06* (2016.02); *G01L 1/246* (2013.01); *G01L 5/166* (2013.01); *A61B 34/35* (2016.02); *A61B 34/72* (2016.02); *A61B 34/76* (2016.02); *A61B 34/77* (2016.02);
(Continued)

(58) Field of Classification Search
CPC .................... A61B 17/00234; A61B 19/2203; A61B 19/30; A61B 19/46; A61B 19/50
USPC ....................... 700/245, 257, 258; 318/568.1
See application file for complete search history.

(56) References Cited

U.S. PATENT DOCUMENTS 5,397,323 A    3/1995  Taylor et al.
5,800,423 A    9/1998  Jensen
(Continued)

FOREIGN PATENT DOCUMENTS

WO    WO-2012/018816 A2    2/2012

OTHER PUBLICATIONS

Balicki et al., "Micro-force sensing in robot assisted membrane peeling for vitreoretinal surgery," in *MICCAI*, 2010, vol. 13, pp. 303-310.

(Continued)

*Primary Examiner* — McDieunel Marc
(74) *Attorney, Agent, or Firm* — Venable LLP; Henry J. Daley

(57) ABSTRACT

A multi-force sensing instrument includes a tool that has a tool shaft having a distal end and a proximal end, a strain sensor arranged at a first position along the tool shaft, at least one of a second strain sensor or a torque-force sensor arranged at a second position along the tool shaft, the second position being more towards the proximal end of the tool shaft than the first position, and a signal processor configured to communicate with the strain sensor and the at least one of the second strain sensor or the torque-force sensor to receive detection signals therefrom. The signal processor is configured to process the signals to determine a magnitude and position of a lateral component of a force applied to the tool shaft when the position of the applied force is between the first and second positions.

18 Claims, 18 Drawing Sheets

(51) Int. Cl.
  *G01L 5/16* (2006.01)
  *G01L 1/24* (2006.01)
  *A61F 9/007* (2006.01)
(52) U.S. Cl.
  CPC .............. *A61B 2017/00345* (2013.01); *A61B 2090/031* (2016.02); *A61B 2090/064* (2016.02); *A61B 2090/065* (2016.02); *A61B 2090/066* (2016.02); *A61B 2560/0247* (2013.01); *A61B 2562/0266* (2013.01); *A61B 2562/0271* (2013.01); *A61F 9/007* (2013.01)

(56) References Cited

U.S. PATENT DOCUMENTS

| | | | |
|---|---|---|---|
| 7,021,173 B2 | 4/2006 | Stoianovici et al. | |
| 7,594,912 B2 | 9/2009 | Cooper et al. | |
| 7,854,742 B2* | 12/2010 | Schachar | A61F 2/147 606/166 |
| 7,930,065 B2* | 4/2011 | Larkin | A61B 19/2203 600/104 |
| 8,361,098 B2* | 1/2013 | Schachar | A61F 2/147 606/166 |
| 8,500,767 B2* | 8/2013 | Schachar | A61F 2/147 606/166 |
| 8,623,037 B2* | 1/2014 | Schachar | A61F 2/147 606/107 |
| 8,852,120 B2* | 10/2014 | Laham | A61B 10/0266 600/562 |
| 9,393,344 B2* | 7/2016 | Stockman | A61K 31/785 |
| 2007/0156019 A1* | 7/2007 | Larkin | A61B 19/2203 600/104 |
| 2011/0178508 A1* | 7/2011 | Ullrich | A61B 19/22 606/1 |
| 2011/0230868 A1* | 9/2011 | Isobe | A61B 17/1626 606/1 |
| 2012/0067354 A1 | 3/2012 | Lammertse | |
| 2012/0132018 A1 | 5/2012 | Tang et al. | |
| 2013/0039732 A1 | 2/2013 | Brewer et al. | |
| 2013/0090763 A1 | 4/2013 | Simaan et al. | |
| 2013/0123798 A1 | 5/2013 | Tsao et al. | |
| 2013/0131867 A1 | 5/2013 | Olds et al. | |
| 2013/0190734 A1 | 7/2013 | Taylor et al. | |
| 2014/0052150 A1 | 2/2014 | Taylor et al. | |
| 2014/0142591 A1 | 5/2014 | Alvarez et al. | |
| 2015/0157191 A1* | 6/2015 | Phee | A61B 1/00133 600/106 |
| 2015/0289946 A1* | 10/2015 | Johansson | G09B 23/285 434/262 |
| 2015/0374449 A1* | 12/2015 | Chowaniec | A61B 19/46 606/1 |

OTHER PUBLICATIONS

Gupta et al., "Surgical forces and tactile perception during retinal microsurgery," in *MICCAI*, 1999, vol. 1679, pp. 1218-1225.
Ida et al., "Microsurgical robotic system for vitreoretinal surgery," IJCARS, vol. 7, No. 1, pp. 27-34, 2012.
International Search Report and Written Opinion of the International Searching Authority in PCT International Application No. PCT/US2015/033322 dated Jul. 24, 2015.
Iordachita et al., "A sub-millimetric, 0.25 mN resolution fully integrated fiber-optic force-sensing tool for retinal microsurgery," IJCARS, vol. 4, No. 4, pp. 383-390, 2009.
Kapoor et al., "Constrained control for surgical assistant robots," IEEE ICRA, 2006, pp. 231-236.
Kumar et al., "Preliminary experiments in cooperative human/robot force control for robot assisted microsurgical manipulation," in IEEE ICRA, 2000, pp. 610-617.
Mitchell et al., "Development and application of a new steady-hand manipulator for retinal surgery," in IEEE ICRA, 2007, pp. 623-629.
Uneri et al., "New Steady-Hand Eye Robot with micro-force sensing for vitreoretinal surgery," in IEEE BioRob, 2010, pp. 814-819.
Wilkins et al., "Characterization of epiretinal membranes using optical coherence tomography.," Ophthalmology, vol. 103, No. 12. pp. 2142-2151, 1996.
Abbott et al., "Virtual fixture architectures for telemanipulation," in *IEEE ICRA*, 2003, pp. 2798-2805.
Berkelman et al., "A miniature instrument tip force sensor for robot/human cooperative microsurgical manipulation with enhanced force feedback," in *MICCAI*, 2000, pp. 897-906.
Bettini et al., "Vision-assisted control for manipulation using virtual fixtures," *IEEE Transactions on Robotics*, vol. 20, No. 6, pp. 953-966, 2004.
Charles et al., "Dexterity-enhanced telerobotic microsurgery," in *IEEE ICRA*, 1997, pp. 5-10.
Cutler et al., "Auditory force feedback substitution improves surgical precision during simulated ophthalmic surgery," *IOVS*, vol. 54, No. 2, pp. 1316-1324, 2013.
He et al., "Toward Clinically Applicable Steady-Hand Eye Robot for Vitreoretinal Surgery," in *ASME 2012 International Mechanical Engineering Congress and Exposition*, 2012, vol. vol. 2:, pp. 213-218.
He et al., "A Sub-Millimetric 3-DOF Force Sensing Instrument with Integrated Fiber Bragg Grating for Retinal Microsurgery," *IEEE TBME*, accepted, 2013.
He et al., "Force sensing micro-forceps with integrated fiber Bragg grating for vitreoretinal surgery," in *SPIE Phontics West*, 2012, 8218-82180W, pp. 1-7.
He et al., "A novel dual force sensing instrument with cooperative robotic assistant for vitreoretinal surgery," in *IEEE ICRA*, 2013, pp. 213-218.
Hubschman et al., "Evaluation of the motion of surgical instruments during intraocular surgery," *Eye (London, England)*, vol. 25, No. 7, pp. 947-953, 2011.
Krupa et al., "Achieving high-precision laparoscopic manipulation through adaptive force control," *Advanced Robotics*, vol. 18, No. 9, pp. 905-926, 2004.
Kummer et al., "OctoMag: an electromagnetic system for 5-DOF wireless micromanipulation," *IEEE Transactions on Robotics*, vol. 26, No. 6, pp. 1006-1017, 2010.
Li et al., "Spatial motion constraints using virtual fixtures generated by anatomy," *IEEE Transactions on Robotics*, vol. 23, No. 1, pp. 4-19, 2007.
Liu et al., "Miniature fiber-optic force sensor based on low-coherence Fabry-Pérot interferometry for vitreoretinal microsurgery," *Biomedical Optics Express*, vol. 3, No. 5, pp. 1062-1076, 2012.
Maclachlan et al., "Micron: an actively stabilized handheld tool for microsurgery," *IEEE Transactions on Robotics*, vol. 28, No. 1, pp. 195-212, 2012.
Marayong et al., "Spatial motion constraints: theory and demonstrations for robot guidance using virtual fixtures," in *IEEE ICRA*, 2003, vol. 2, pp. 1954-1959.
Menciassi et al., "Force feedback-based microinstrument for measuring tissue properties and pulse in microsurgery," in *IEEE ICRA*, 2001, pp. 626-631.
Murray et al., *A Mathematical Introduction to Robotic Manipulation*, CRC Press, 1994.
Nakano et al., "A parallel robot to assist vitreoretinal surgery," *IJCARS*, vol. 4, No. 6, pp. 517-526, 2009.
Patkin, "Ergonomics applied to the practice of microsurgery.," *The Australian and New Zealand Journal of Surgery*, vol. 47, No. 3, pp. 320-329, 1977.
Peirs et al., "A micro optical force sensor for force feedback during minimally invasive robotic surgery," *Sensors and Actuators A: Physical*, vol. 115, No. 2-3, pp. 447-455, 2004.
Polygerinos et al., "MRI-compatible intensity-modulated force sensor for cardiac catheterization procedures," *IEEE TBME*, vol. 58, No. 3, pp. 2598-2603, 2011.
Puangmali et al., "Miniature 3-Axis Distal Force Sensor for Minimally Invasive Surgical Palpation," *IEEE/ASME Transactions on Mechatronics*, vol. 17, No. 4, pp. 646-656, 2012.

(56) References Cited

OTHER PUBLICATIONS

Rosenberg, "Virtual fixtures: Perceptual tools for telerobotic manipulation," in *IEEE Virtual Reality Annual International Symposium*, 1993, pp. 76-82.
Seibold et al., "Prototype of Instrument for Minimally Invasive Surgery with 6-Axis Force Sensing Capability," in *IEEE ICRA*, 2005, pp. 498-503.
Song et al., "Fiber-optic OCT sensor guided 'SMART' micro-forceps for microsurgery," *Biomedical Optics Express*, vol. 4, No. 7, pp. 1045-1050, 2013.
Taylor et al., "A Steady-Hand Robotic System for Microsurgical Augmentation," *The IJRR*, vol. 18, No. 12, pp. 1201-1210, 1999.
Wei et al., "Design and theoretical evaluation of micro-surgical manipulators for orbital manipulation and intraocular dexterity," in *IEEE ICRA*, 2007, pp. 3389-3395.
Yu et al., "Design , Calibration and preliminary testing of a robotic telemanipulator for OCT guided retinal surgery," in *IEEE ICRA*, 2013, pp. 225-231.

\* cited by examiner

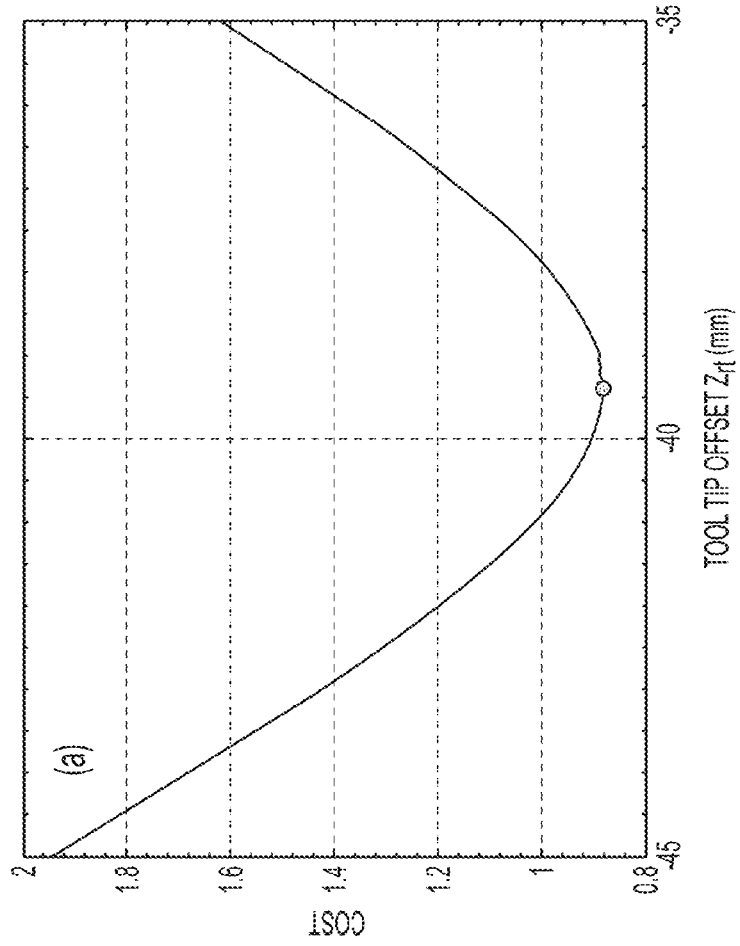
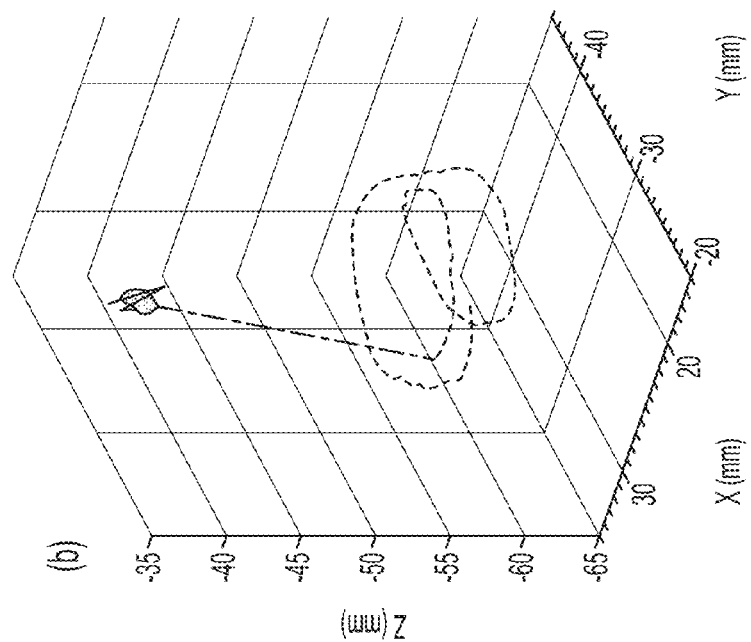
FIG. 15B
FIG. 15A

MULTI-FORCE SENSING SURGICAL INSTRUMENT AND METHOD OF USE FOR ROBOTIC SURGICAL SYSTEMS

FEDERAL FUNDING

This invention was made with Government support of Grant No. R01 EB 000526 and BRP Grant 1 R01 EB 007969, awarded by the Department of Health and Human Services, The National Institutes of Health (NIH). The U.S. Government has certain rights in this invention.

BACKGROUND

1. Field of Invention

The field of the currently claimed embodiments of this invention relates to multi-force sensing instruments, robotic systems that incorporate the instruments, and methods of use.

2. Discussion of Related Art

Retinal microsurgery refers to intraocular surgical treatment of disorders related to the retina, vitreous, and macula of the eye. Typical diseases include retina detachment, macular degeneration, and diabetic retinopathy. Retinal microsurgery demands advanced surgical skills that are near or beyond natural human capabilities. During retinal microsurgery, a surgical microscope is placed above the patient to provide magnified visualization of the interior of the eye. The surgeon inserts small instruments (e.g. 25 Ga) through trocars on the sclera, the white part of the eye, to perform delicate tissue manipulation in the posterior of the eye.

An example of a common surgical task is epiretinal membrane (ERM) peeling to restore the patient's vision from ERM distortion. The surgeon carefully peels the thin, semi-transparent scar tissue (the ERM) off the retina using a micro-forceps, as shown in FIGS. 1A and 1B. Steady and precise motion is desired, because the thickness of the ERM 1 can be an order of magnitude smaller than human hand tremor 2. Additionally the force applied on the ERM has to stay below the strength of the retina tissue. However, the forces exerted between the instrument tip and the retina are well below the human sensory threshold 1. The absence of force sensing raises the risk of applying excessive force on the retina, which can potentially cause retina hemorrhage and tearing. During the ERM peeling, the eye should be stable to minimize the motion of the target membrane. This requires the tool motion to comply at the sclerotomy site. Only three rotational degrees of freedom (DOF) about the sclera entry point and one translational DOF along the instrument axis are allowed, while lateral translations are prohibited by the sclera constraint. This corresponds to the concept of remote center-of-motion (RCM) in robotics, devised by Taylor et al. 4. A fixed RCM is often considered to be a fundamental requirement in minimally invasive Surgery (MIS).

Unlike MIS, the imaging component of retinal microsurgery, the microscope, is located outside the patient and is rarely moved, as shown in FIG. 1A. Instead, the retinal surgeon needs to reposition the patient's eye while the tools are inserted, in order to adjust the view and gain tool access to the region of interest. As a result, the location of the RCM point (the sclera entry point) is not necessarily fixed, and can move up to 12 mm during retinal microsurgery 5. The repositioning of the eye requires all of the instruments inserted in the eye (e.g. a micro-forceps and a light pipe) to move in coordination. Unsynchronized instrument motion can cause cornea striae, which distorts the view of the retina in the microscope. Suboptimal ergonomics and fatigue impose further limitations on surgical performance.

Many robotic systems have been developed and investigated to explore the potential to enhance and expand the capabilities of retinal surgery and microsurgery in general. Master-slave teleoperated robotic systems 6-10 have the advantage of motion scaling to achieve high precision. Building both master and slave robots results in complex systems and high cost. Furthermore, the surgeon's perception of the interaction between the slave robot and the patient is inadequate. Another approach is handheld robotic devices that provide active tremor cancellation 1112. Despite increased size and weight attributed to additional actuators, these devices provide an intuitive interface. However, the workspace is constrained by the tracking system and scaled feedback of the human-imperceptible forces cannot be implemented. The third approach is untethered micro-robots moved by controlled nonuniform magnetic fields 13. The untethered control enables a large workspace and complex maneuvers. The drawbacks include the large footprint and limited surgical application.

Some embodiments of the current invention can use the Steady-Hand Eye Robot with hands-on cooperative control 14-17, where the user and the robot both hold the surgical instrument. The user input force applied on the instrument handle controls the velocity with which the robot follows the user motion. This control approach is also termed admittance velocity control. The human hand tremor is damped by the stiff robot structure. The cooperatively controlled robot provides not only the precision and sensitivity of a machine, but also the manipulative transparency and immediacy of hand-held instruments. This robotic system can further be augmented with virtual fixtures 18, as well as incorporated with smart instruments with various sensing modalities.

Virtual fixtures are algorithms that provide assistive motion guidance with anisotropic robot behavior. The robot motion constraints assist the user to avoid forbidden regions 1819, as well as to guide along desired paths 2021. Virtual fixtures can be prescribed 1819, generated from patient anatomy 22 or from real-time computer vision 20. The implementation includes impedance 19 and admittance methods 2021, as well as optimization algorithms with desired geometric constraints 2223. With the aid of virtual fixtures, the mental and physical demands on the user to accomplish a desired maneuver are reduced, while the task performance is notably increased. The surgeon can concentrate on the critical surgical tasks (e.g. ERM peeling) if virtual fixtures can manage the inherent surgical motion constraints, such as RCM and tool coordination, by providing an intuitive, guided robot behavior.

Smart instruments with force sensing capability are essential for safe interaction between the robot and the patient. Various force sensors have been developed for microsurgery, micromanipulation, and MIS 24-28. Handle mounted force sensors 29 cannot distinguish forces exerted at the tool tip from those at the trocar. Therefore, a family of force sensing instruments 30-33 has been developed with fiber optic sensors integrated into the distal portion of the instrument that is typically located inside the eye. Auditory 34 and haptic 35 force feedbacks have demonstrated the efficacy of regulating the tool-to-tissue interaction force. During a freehand manipulation, the surgeon can often sense the contact force at the sclera entry point, and utilizes it as an important indicator to guide the desired motion, e.g. RCM and tool coordination. However, the stiffness of the Steady-Hand Eye Robot attenuates the user perceptible level of the sclera force, inducing undesired large sclera forces. We devised a dual force sensing instrument 36 to provide force feedback from both tool tip force and sclera force. The drawback is that the force sensor cannot provide the sclera force value and the location where the sclera force is applied on the tool shaft. Instead, it measures the moment attributed to the sclera force. Therefore, there remains a need for multi-force sensing instruments, robotic systems that incorporate the instruments, and methods of use.

SUMMARY

A multi-force sensing instrument according to some embodiments of the current invention includes a tool that has a tool shaft having a distal end and a proximal end, a strain sensor arranged at a first position along the tool shaft, at least one of a second strain sensor or a torque-force sensor arranged at a second position along the tool shaft, the second position being more towards the proximal end of the tool shaft than the first position, and a signal processor configured to communicate with the strain sensor and the at least one of the second strain sensor or the torque-force sensor to receive detection signals therefrom. The signal processor is configured to process the signals to determine a magnitude and position of a lateral component of a force applied to the tool shaft when the position of the applied force is between the first and second positions. The lateral component of the force is a component of the force that lies in a plane that is orthogonal to the tool shaft at the position at which the force is applied.

A robotic system according to some embodiments of the current invention includes a robot having a tool connector, a multi-force sensing instrument attached to the tool connector of the robot, and a feedback system configured to communicate with the multi-force sensing instrument to provide at least one of feedback control of the robot or feedback information to a user of the robotic system. The multi-force sensing instrument includes a tool that has a tool shaft having a distal end and a proximal end, a strain sensor arranged at a first position along the tool shaft, at least one of a second strain sensor or a torque-force sensor arranged at a second position along the tool shaft, the second position being more towards the proximal end of the tool shaft than the first position, and a signal processor configured to communicate with the strain sensor and the at least one of the second strain sensor or the torque-force sensor to receive detection signals therefrom. The signal processor is configured to process the signals to determine a magnitude and position of a lateral component of a force applied to the tool shaft when the position of the applied force is between the first and second positions. The lateral component of the force is a component of the force that lies in a plane that is orthogonal to the tool shaft at the position at which the force is applied.

A method of controlling a robotic system according to some embodiments of the current invention includes performing an action with a multi-force sensing instrument. The multi-force sensing instrument includes a tool that has a tool shaft having a distal end and a proximal end, a strain sensor arranged at a first position along the tool shaft, at least one of a second strain sensor or a torque-force sensor arranged at a second position along the tool shaft, the second position being more towards the proximal end of the tool shaft than the first position, and a signal processor configured to communicate with the strain sensor and the at least one of the second strain sensor or the torque-force sensor to receive detection signals therefrom. The signal processor is configured to process the signals to determine a magnitude and position of a lateral component of a force applied to the tool shaft when the position of the applied force is between the first and second positions. The lateral component of the force is a component of the force that lies in a plane that is orthogonal to the tool shaft at the position at which the force is applied. The method also includes providing control signals to a robot based on the magnitude and position of the lateral component of the force determined from the multi-force sensing instrument such that the robot performs an automatic action in response thereto.

BRIEF DESCRIPTION OF THE DRAWINGS

Further objectives and advantages will become apparent from a consideration of the description, drawings, and examples.

FIGS. 15A and 15B show results of the optimization to find the tool tip offset from the handle along Z-axis (a). The optimum offset is at $z^*_{rt}$=−39.4 mm, shown as the dot. The corresponding trajectories of the RCM point (top) and the tool tip (bottom) (b). The black straight line shows the end position of the tool shaft.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Currently, there are a few robotics systems for the surgeries that involve inserting surgical instruments through access ports to perform manipulation inside the patient. The port location with respect to the instrument is important because the tool motion is constrained at the port. The contact force between the port and the tool shaft distorts the surgeon's perception of the tool-to-tissue interaction force exerted at the tool tip. Appropriate solutions to these challenges are still lacking.

Some embodiments of the current invention provide systems and methods to integrate multi-function force sensing into surgical instruments. It can precisely measure the location of the contact point between the tool shaft and the port, the contact force, as well as the force exerted at the tool tip. The force information can be presented directly to the surgeon using visual or aural display, or used in a robotic surgical system to provide useful feedback and intuitive motion guidance for various surgical procedures.

An embodiment of the current invention provides a new dual force sensing instrument that can sense not only the sclera force in transverse directions, but also the location of the sclera contact point on the tool shaft. This new dual force sensing instrument can enable a variable admittance robot control to provide intuitive robot behavior. By varying the robot admittance, the robot behavior can continuously transit from an adaptive virtual fixture mode that enforces RCM and adapts to the current location of the sclerotomy site, to a force scaling mode that provides scaled feedback of the sclera force as well as the ability to reposition the eye. Experiments have been conducted to calibrate the new dual force sensing instrument, to calibrate the tool tip position with respect to the robot, and to evaluate the force sensor as well as the control algorithm according to an embodiment of the current invention. The results show the potential to increase safety, as well as to enhance the usability and capability of such a robotic assistant system.

Figure 1B:
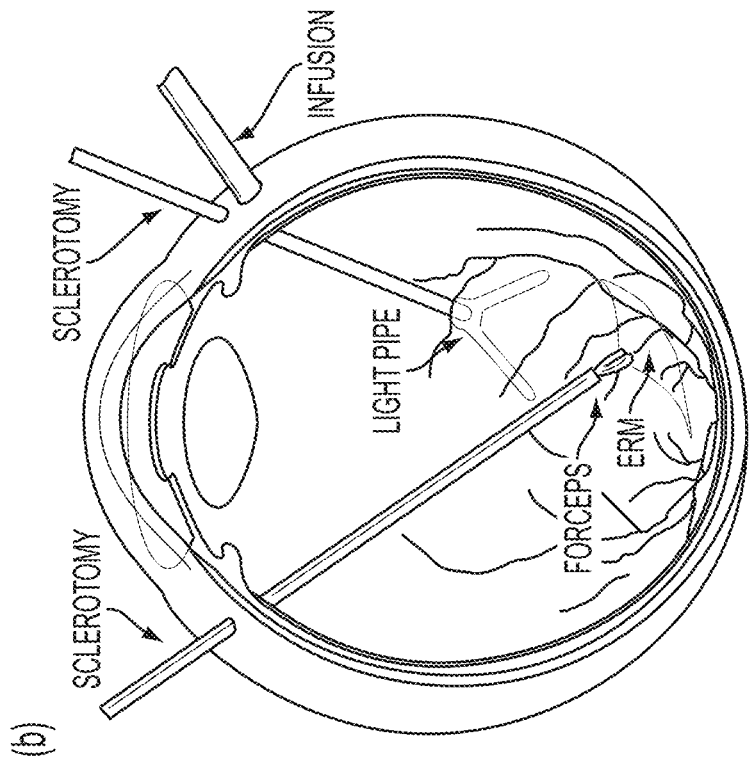
FIGS. 1A and 1B show an example of retinal microsurgery: (a) position of the patient and the lead surgeon in the operating room; and (b) the layout of the surgical instruments in the eye during ERM peeling.
Figure 1A:
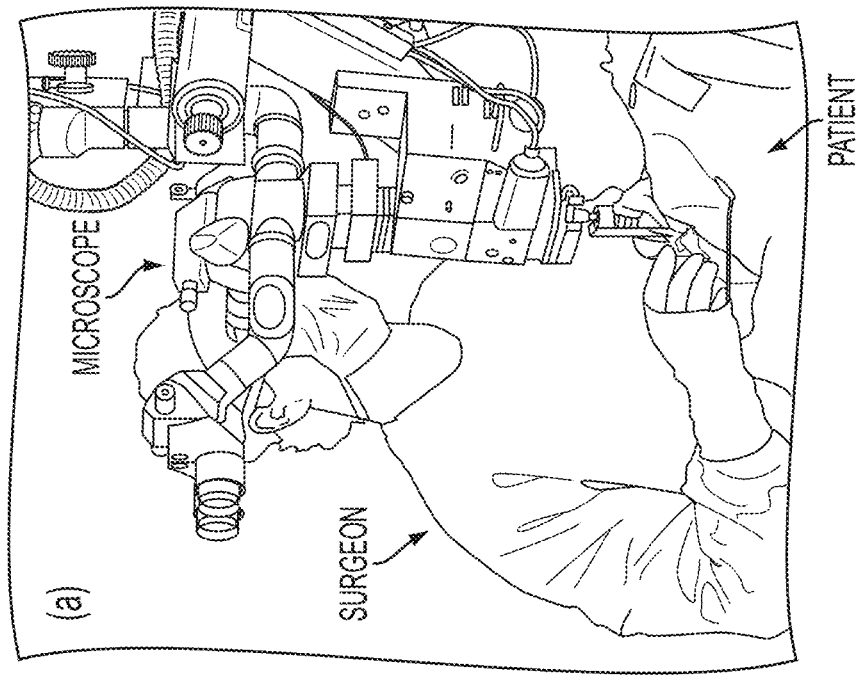
Figures 2A, 2B, 2C, 2D:
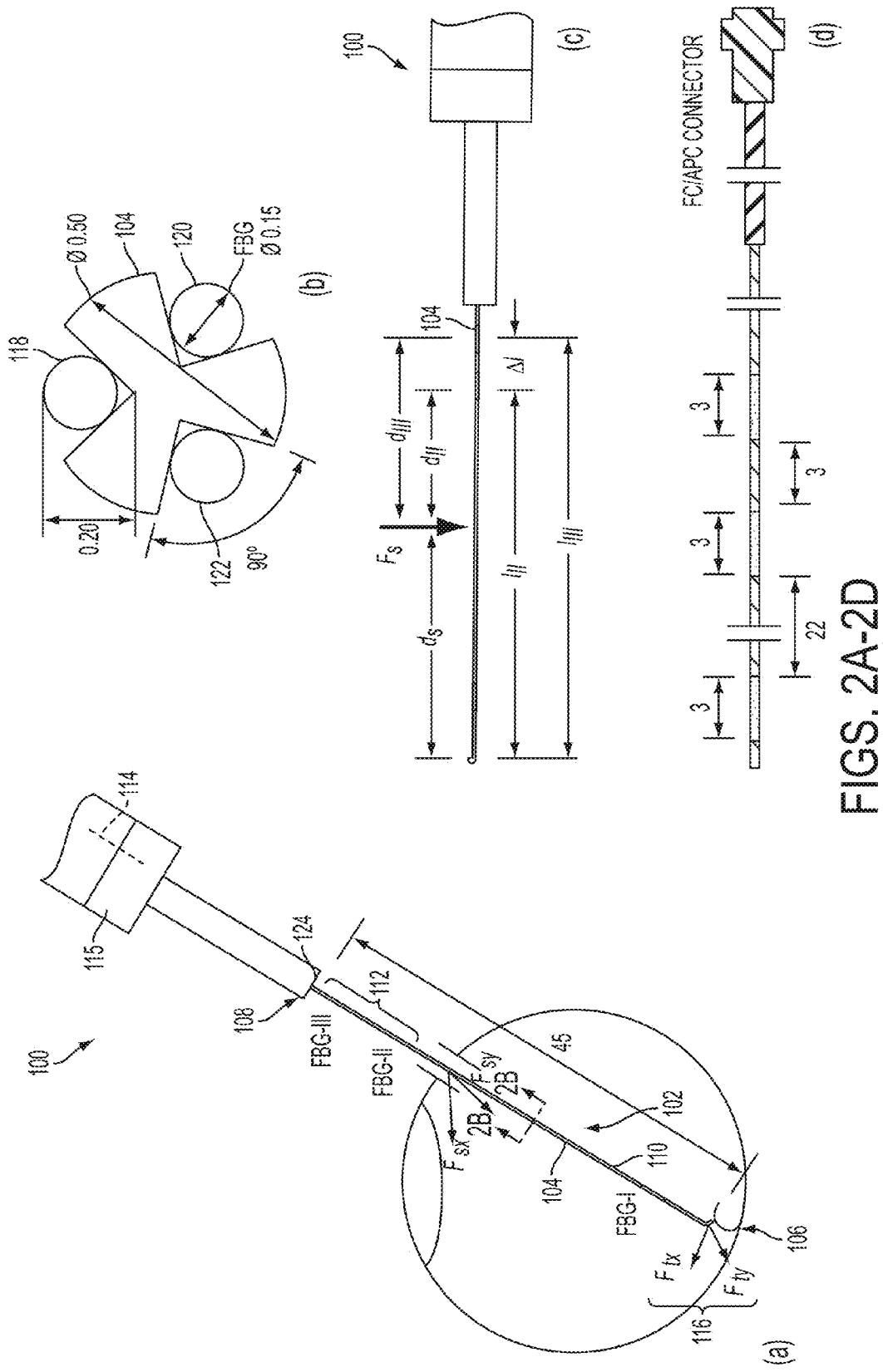
FIGS. 2A-2D illustrate an embodiment of a multi-force sensing instrument according to an embodiment of the current invention. Dimensions of an example of a multi-function force sensing instrument are shown in (a). The section view of the tool shaft with the FBG sensors (b). The geometry related to tool calibration (c). The dimension of a single fiber with three FBG sensors (d). The center Bragg wavelengths of FBG-I, FBG-II, and FBG-III are 1529 nm, 1545 nm, and 1553 nm, respectively.

FIG. 2A provides an illustration of a multi-force sensing instrument 100 according to an embodiment of the current invention. The multi-force sensing instrument 100 includes a tool 102 that has a tool shaft 104 having a distal end 106 and a proximal end 108. The multi-force sensing instrument 100 also includes a strain sensor 110 arranged at a first position along the tool shaft 104, and at least one of a second strain sensor 112 or a torque-force sensor (not shown in FIG. 2A) arranged at a second position along the tool shaft 104. The second position corresponding to the second strain sensor 112 is more towards the proximal end 108 of the tool shaft 104 than the first position corresponding to the strain sensor 110.

The multi-force sensing instrument 100 also includes signal processor 114 configured to communicate with the strain sensor 110 and the at least one of the second strain sensor or the torque-force sensor 112 to receive detection signals therefrom. The signal processor 114 is configured to process the signals to determine a magnitude $F_s$ and position $d_s$ of a lateral component of a force applied to the tool shaft 104 when the position $d_s$ of the applied $F_s$ force is between the first and second positions, as is illustrated in FIG. 2C. The lateral component of the force is a component of the force that lies in a plane that is orthogonal to the tool shaft 104 at the position at which the force is applied.

The signal processor 114 can be incorporated within a tool handle 115 of the tool 102, as illustrated in FIG. 2A. However, the invention is not limited to this example. It could be incorporated into a different portion of the tool 102 and/or located externally. The signal processor can include and/or access memory and/or data storage. The signal processor can be a programmable device and/or a dedicated hard-wired device, such as, but not limited to an ASIC or FPGA.

Figure 3:
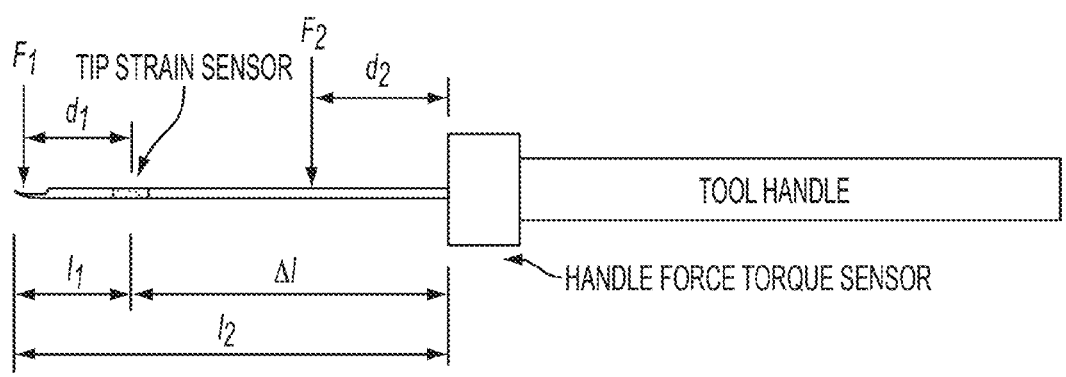
FIG. 3 is a schematic illustration of a multi-force sensing instrument according to another embodiment of the current invention.

The multi-force sensing instrument 100 can include a wide range of tools 102, as long as they have a structure corresponding to the shaft 104. The tool 102 can be, but is not limited to a surgical tool. FIG. 3 is an illustration in which two different embodiments of multi-force sensing instruments according to the current invention are being used for eye surgery. Other applications can include other form of micromanipulation in which a tool is extended through a narrow opening in a structure. More generally, some embodiments can include tools that are used to extend through a larger opening in larger structures. Examples of micromanipulation tools can include, but are not limited to needles, forceps, picks, cannulas, trocars, catheters, guide wires, light pipes, endoscopes, etc.

In some embodiments, the signal processor 114 can be further configured to process the signals to determine a magnitude and position of a distal force 116 applied to the tool shaft 104 when the position of the distal force is beyond the first position towards the distal end 106 of the tool shaft 104.

In some embodiments, the second strain sensor 112 can be a pair of strain sensors displaced with respect to each other along a distal to proximal axial direction along said tool shaft. Furthermore, the first-mentioned strain sensor 110 and the pair of strain sensors 112 can include at least one optical fiber. In that case, the optical fiber includes first, second and third Fiber Bragg Gratings (FBG-I, FBG-II, FBG-III) written therein corresponding respectively to said first-mentioned strain sensor 110 and the pair of strain sensors 112 in which the optical fiber extends substantially parallel to the tool shaft 104. The term "substantially parallel" is intended to convey the fact that the fiber does not have to be perfectly parallel. In some cases, there may be deviations due to manufacturing tolerances. In some cases, a high degree of precision may not be required for the application, so a degree of erro can be accepted.

Although particular embodiments describe the strain sensors as FGBs in optical fibers, the general concepts of the current invention are not limited to only FBGs. Other types of strain sensors can be used without departing from the broad scope of the current invention.

In some embodiments, the first-mentioned strain sensor 110 and the pair of strain sensors 112 include a plurality of optical fibers (for example, 118, 120, 122 in FIG. 2B) each comprising first, second and third Fiber Bragg Gratings (FBG-I, FBG-II, FBG-III) written therein corresponding respectively to the first-mentioned strain sensor 110 and the pair of strain sensors 112. The plurality of optical fibers (e.g., 118, 120, 122) each extend substantially parallel to the tool shaft 104 and substantially parallel to each other. Although FIG. 2B illustrates an embodiment with three optical fibers, the plurality of optical fibers is not limited to that particular number. In some embodiments, there could be two, three or more than three optical fibers. The plurality of optical fibers (e.g., 118, 120, 122) can be arranged substantially equally spaced around a circumference of the tool shaft 104. In the case of three optical fibers, FBG-I, FBG-II, FBG-III each includes a set of three fiber Bragg gratings. In the embodiment of FIG. 2B, the plurality of optical fibers (118, 120, 122) are three optical fibers oriented about 120° apart around a circumference of the tool shaft 104. The dimensions illustrated in FIGS. 2A-2D are for a particular embodiment and are not required in all embodiments.

The embodiment of FIGS. 2A-2D can be useful for being able to determine two force components within the plane orthogonal to the tool shaft 104 as well as being able to compensate for temperature changes.

In some embodiments, the first, second and third Fiber Bragg Gratings (FBG-I, FBG-II, FBG-III) written in the optical fiber, or fibers, can each have a unique central reflection wavelength under relaxed, equal temperature conditions to allow wavelength division multiplexing within the optical fiber.

The multi-force sensing instrument 100 can also include at least one optical transmitter and at least one optical receiver 124 optically coupled to the one or more optical fiber. The optical transmitter(s) and receiver(s) 124 can be incorporated into the tool handle 115, as is illustrated in FIG. 2A, or can be located externally. Optical transmitters can include, but are not limited to, LEDs and semiconductor lasers, for example. The optical receivers can include, but are not limited to, photodiodes, for example.

Figure 4:
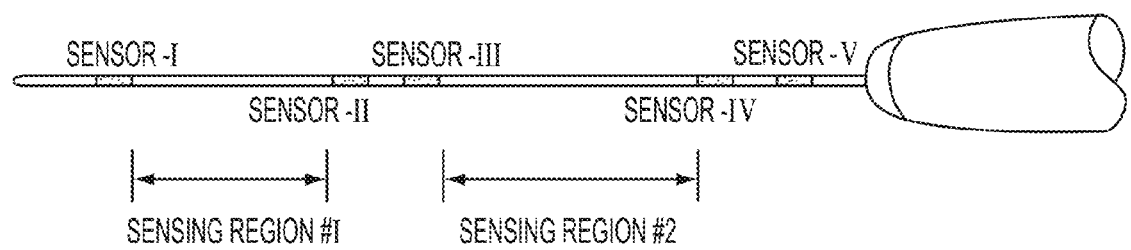
FIGS. 4, 5A and 5B are schematic illustrations of further embodiments of multi-force sensing instruments according to the current invention.
Figures 5A, 5B:
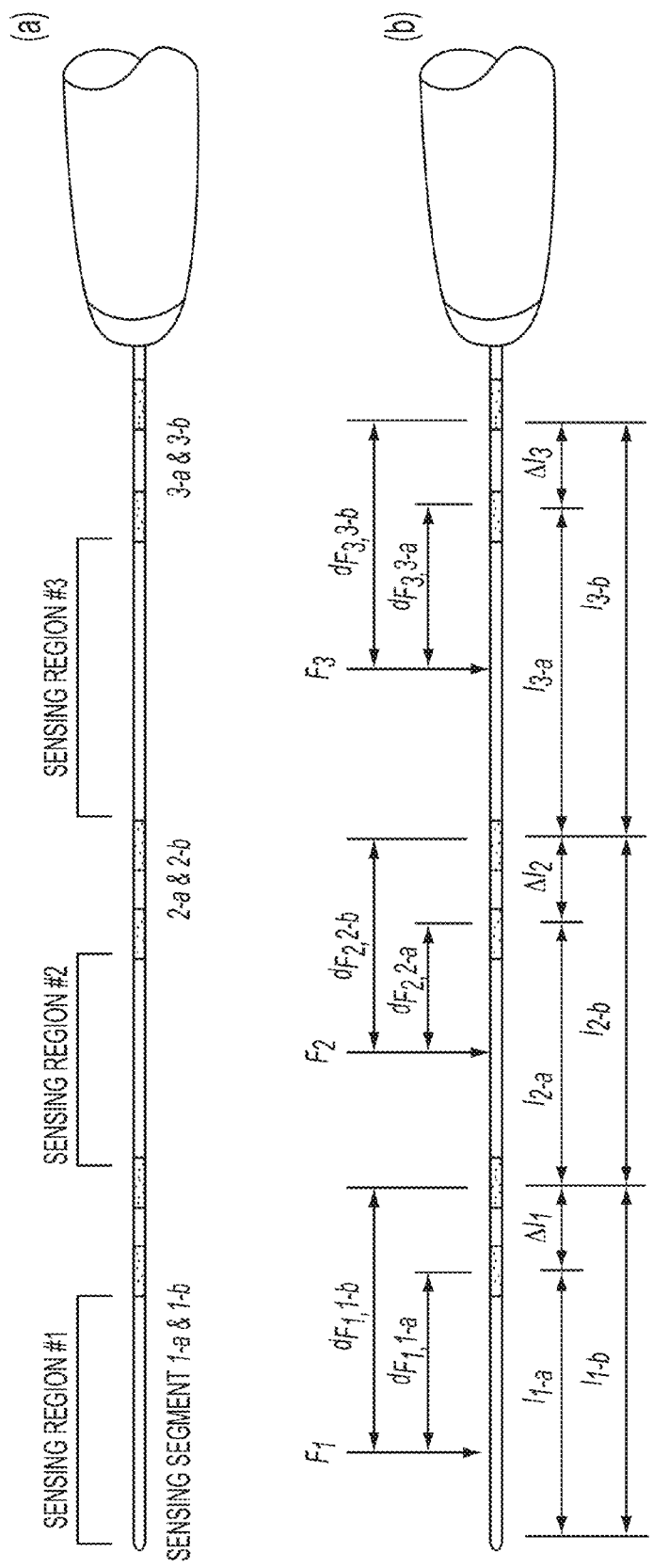

FIGS. 4, 5A and 5B illustrate additional embodiments in which multiple strain sensors can be included to set up a plurality of sensing regions. The general concepts of the current invention are not limited to the particular number of sensing regions. For example, some embodiments could have a large number of closely spaced sensing regions to approximate a continuous sensing capability along the tool shaft.

The following provides a formalism for a general number of sensing segments and groups. Note that above we referred to a sensor in reference to FBG pairs, i.e., groups. Furthermore, if there are three optical fibers, each FBG pair (or group) would have 6 sensing elements. FIG. 5A illustrates one example with six sensing segments in three groups. Multiple sensing segments can enable the sensor to measure multiple contact forces and their locations on the tool shaft. The assumption is that at most one contact force is applied within each sensing region. If the fiber optical strain sensor, fiber Bragg grating (FBG), is used as the strain sensor, then this extension does not require additional space for incorporating extra sensors. The multi-function sensing instrument can preserve the same form factor.

One example of a generalized model is illustrated in FIGS. 5A and 5B that has six sensing segments, shown as 1-$a$ and 1-$b$ to 3-$a$ and 3-$b$. Each sensing segment includes three strain sensors that are evenly placed around the circumference of the tool shaft, with 120° intervals. The strain sensors in this example are optical strain gauges based on fiber Bragg gratings (FBGs). A group of two sensing segments separates the sensing regions on the tool shaft. The sensing segments are numbered with the Arabic numerals indicating the sensing region, adjoint with -a or -b for the distal and proximal one within the group. For example, 1-$b$ denotes the proximal sensing segment in the first group, as shown in FIG. 5A. The portion of the tool shaft that is located between the sensing segments are called sensing regions, numbered with the Arabic numerals. We assume there is at most one contact force exerted within one sensing region. The contact forces are also numbered with Arabic numerals. The distance between force $F_i$ and sensing segment j-x is denoted as $d_{Fi,j-x}$, where i=1, 2, . . . , j=1, 2 . . . , and x=a or b. The constant distance between the two sensors within the same group, sensing segments j-a and j-b, is denoted as $\Delta l_j$, where j=1, 2, . . . , and we have $\Delta l_j = l_{j-b} - l_{j-a} = d_{Fi,j-b} - d_{Fi,j-b}$, for any $F_i$ that is distal to sensing segment j, i.e. i≤j. One special case of the first contact force $F_1$ is the tool-to-tissue interaction force exerted right at the tool tip, i.e. $d_{F1,1-x} = l_{1-x}$, x=a or b.

First, we look at one strain sensor within each sensing segment. When transverse force is applied to the tool shaft, the strain generated is proportional to the moment at the sensor location and thus proportional to the force applied:

$$\epsilon = \frac{M}{EI}r = \frac{Fd}{EI}r \tag{1}$$

where $\epsilon$ is the local strain at the sensor location, M is the moment at the sensor location that is attributed to the transverse force, F is the transverse force applied to the tool shaft, d is the distance between the force and the sensor location, i.e. the moment arm, E is the Young's modulus, I is the moment of inertia, and r is the radial distance between the bending axis and the strain sensor.

The shift in Bragg wavelength of the FBG sensors is proportional to local strain and temperature change:

$$\Delta\lambda = k_\epsilon \epsilon + k_{\Delta T} \Delta T \quad (2)$$

where $\Delta\lambda$ denotes the shift in the Bragg wavelength of the FBG sensor, $\epsilon$ denotes the local strain at the sensor location, $\Delta T$ denotes the temperature change, $k_\epsilon$ and $k_{\Delta T}$ are constant coefficients.

Second, there are three strain sensors within each sensing segment, evenly placed around the circumference of the tool shaft with 120° intervals. The common mode of the three strain sensors within the same sensing segment is caused mostly by the axial strain and the temperature change. It is the mean value of the wavelength shifts of the three FBG sensors. The remaining differential mode reflects the strain attributed to the transverse forces. We define the differential mode as the sensor reading. It can be calculated by subtracting the common mode from the FBG wavelength shifts:

$$\Delta s_{j-x,k} = \Delta\lambda_{j-x,k} - \frac{1}{3}\sum_{k=1}^{3}\Delta\lambda_{j-x,k} \quad (3)$$

where $\Delta s_{j-x,k}$ and $\Delta\lambda_{j-x,k}$ denote respectively the sensor reading and the wavelength shift of the FBG k in the sensing segment j-x, with j=1, 2, ..., x=a, b, and k=1, 2, 3.

There are two sensing segments longitudinally configured proximal to the corresponding sensing region. With the assumption that $F_1$ is always exerted within the sensing region #1, the sensor readings of sensing segment 1-a and 1-b are linearly dependent on $F_1$:

$$\Delta S_{1-x} = K_{1-x,F_1} M_{F_1,1-x} \quad (4)$$

$$= K_{1-x,F_1} F_1 d_{F_1,1-x} \quad (5)$$

where $\Delta S_{1-x} = [\Delta s_{1-x,1}, \Delta s_{1-x,2}, \Delta s_{1-x,3}]^T$, x=a and b, denote the sensor readings of sensing segment 1-a and 2-b, respectively, $K_{1-x,F_1}$ are the constant coefficient matrices that can be obtained through calibration, and $M_{F_1,1-x}$ denotes the moment at sensing segment 1-x attributed to force $F_1$, i.e.

$$M_{F_1,1-x} = F_1 d_{F_1,1-x} \quad (6)$$

where $F_1 = [F_{1x}, F_{1y}]^T$ denotes the transverse force exerted within the first sensing region, from the tool tip to the first sensing segment, and $d_{F_1,1-x}$ denotes the longitudinal distance from $F_1$ to sensing segment 1-x.

From (4), we can compute the moments attributed to $F_1$ at sensing segment 1-a and 1-b:

$$M_{F_1,1-x} = K_{1-x,F_1}^\dagger \Delta S_{1-x}$$

where $(\bullet)^\dagger$ denotes the matrix pseudo-inverse, x=a and b.

Further we can write:

$$M_{F_1,1-b} - M_{F_1,1-a} = K_{1-b,F_1}^\dagger \Delta S_{1-b} - K_{1-a,F_1}^\dagger \Delta S_{1-a} \quad (8)$$

Also from (7), we can write:

$$M_{F_1,1-b} - M_{F_1,1-a} = F_1(d_{F_1,1-b} - d_{F_1,1-a}) \quad (9)$$

$$= F_1 \Delta l_1 \quad (10)$$

Then we can calculate $F_1$ from (8) and (10)

$$F_1 = \frac{M_{F_1,1-b} - M_{F_1,1-a}}{\Delta l_1} \quad (11)$$

$$= \frac{K_{1-b,F_1}^\dagger \Delta S_{1-b} - K_{1-a,F_1}^\dagger \Delta S_{1-a}}{\Delta l_1} \quad (12)$$

The distance from $F_1$ to sensing segment 1-x can then be calculated as follows:

$$d_{F_1,1-x} = \frac{\|M_{F_1,1-x}\|}{\|F_1\|} \quad (13)$$

where $\|\bullet\|$ denotes the 2-norm of a vector.

The sensor readings of sensing segments 2-a and 2-b reflect the strain attributed to all forces distal to the sensing segments, i.e. both $F_1$ and $F_2$ contribute to the sensor reading $\Delta S_{2-x}$:

$$\Delta S_{2-x} = K_{2-x,F_1} M_{F_1,2-x} + K_{2-x,F_2} M_{F_2,2-x} \quad (14)$$

$$= K_{2-x,F_1} F_1 d_{F_1,2-x} + K_{2-x,F_2} F_2 d_{F_2,2-x} \quad (15)$$

where $K_{2-x,F_1}$ and $K_{2-x,F_2}$ are constant coefficient matrices that can be obtained through calibration, $M_{F_i,2-x}$ is the moment attributed to force $F_i$ at sensing segment 2-x, i=1 and 2. From (11) and (13), we can calculate $F_1$ and $d_{F_1,1-x}$. In addition, we have:

$$d_{F_1,2-x} = d_{F_1,1-b} + l_{2-x}, \quad (16)$$

as shown in FIGS. 5A and 5B.

Therefore, we can write:

$$M_{F_2,2-x} = K_{2-x,F_2}^\dagger (\Delta S_{2-x} - K_{2-x,F_1} M_{F_1,2-x}) \quad (17)$$

$$= K_{2-x,F_2}^\dagger (\Delta S_{2-x} - K_{2-x,F_1} F_1 d_{F_1,2-x}) \quad (18)$$

$$= K_{2-x,F_2}^\dagger (\Delta S_{2-x} - K_{2-x,F_1} F_1 (d_{F_1,1-b} + l_{2-x})) \quad (19)$$

Similarly, we can calculate $F_2$:

$$F_2 = \frac{M_{F_2,2-b} - M_{F_2,2-a}}{\Delta l_2} \quad (20)$$

and $d_{F_2,2-x}$:

$$d_{F_2,2-r} = \frac{\|M_{F_2,2-x}\|}{\|F_2\|} \quad (21)$$

Now we can derive the equations to calculate $F_j$ and $d_{F_j,j-x}$ based on the steps above. The sensor readings reflect all forces distal to the sensing segment j-x, where j≥2, x=a and b:

$$\Delta S_{j-x} = \sum_{k=1}^{j-1} K_{j-x,F_k} M_{F_k,j-x} + K_{j-x,F_j} M_{F_j,j-x} \quad (22)$$

$$= \sum_{k=1}^{j-1} K_{j-x,F_k} d_{F_k,j-x} + K_{j-x,F_j} M_{F_j,j-x} \quad (23)$$

$$= \sum_{k=1}^{j-1} \left( K_{j-x,F_k} F_k \left( d_{F_k,k-b} + \sum_{i=k+1}^{j} l_{i-x} \right) \right) + K_{j-x,F_j} M_{F_j,j-x} \quad (24)$$

Then the transverse contact force $F_j$ applied within sensing region #j and the distance $d_{F_j,j-x}$ from $F_j$ to sensing segment j-x can be calculated as follows:

$$F_j = \frac{M_{F_j,j-b} - M_{F_j,j-a}}{\Delta l_j} \quad (25)$$

$$d_{F_j,j-x} = \frac{\|M_{F_j,j-x}\|}{\|F_j\|} \quad (26)$$

Smart Light Pipe

Figure 2E:
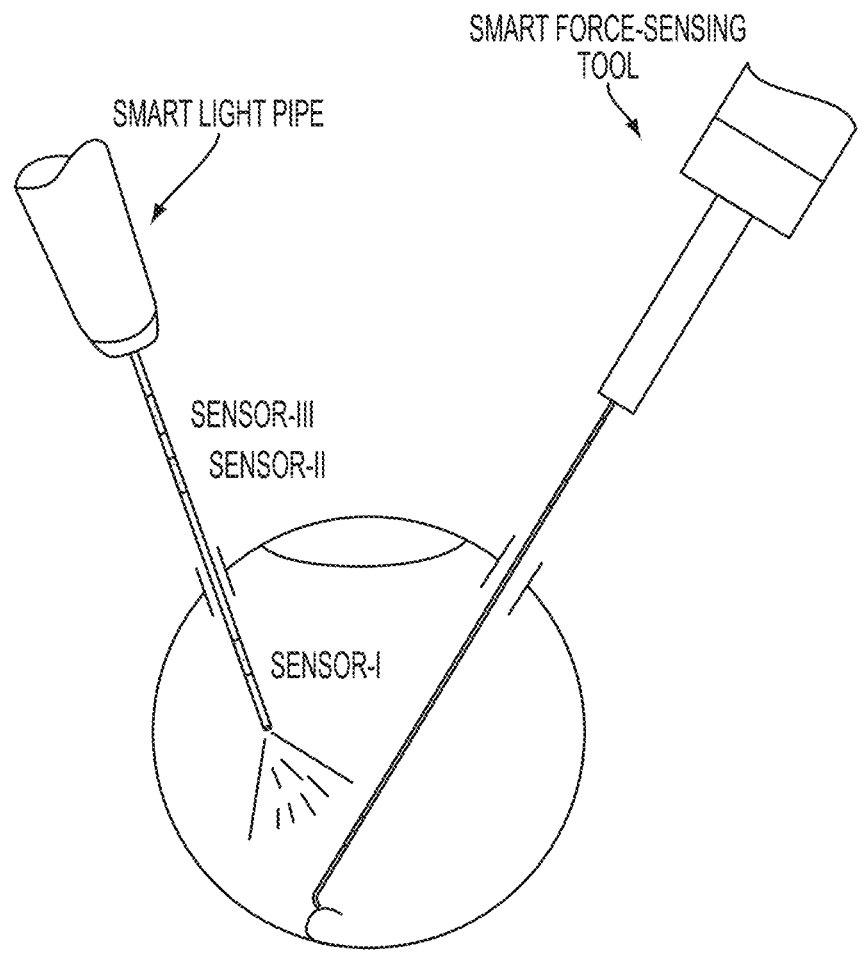
FIG. 2E is a schematic illustration of two multi-force sensing instruments according to embodiments of the current invention being used in conjunction for retinal surgery.

One useful application can be a sensorized light pipe for ophthalmological surgery, as shown in FIG. 2E. Sensor-I can be used for collision detection with other tools, with the lens, or with the retina, etc. Sensor-II and Sensor-III can be used to measure the location of the sclerotomy site and the contact force between the light pipe and the trocar. In current practice of ophthalmological surgery, the surgeon uses one hand to hold a functional tool, e.g. forceps, while the other hand holds a light pipe to provide illumination inside the eye. The sensorized light pipe can be held by a robot, so that the surgeon can perform bilateral manipulation using two instruments, e.g. two forceps.

This can be especially useful during vitrectomy, as well as during complex manipulation of eye tissue. The robot holds the sensorized light pipe, and complies with the eye motion to satisfy the remote center of motion (RCM) constraint. Furthermore, computer vision techniques can be used to track the other tools inside the eye and the lighting history of the eye to adjust position and orientation of the light pipe to provide optimal lighting with minimal light toxicity.

Additional Embodiments

Other sensing implementations can achieve the same functionality of the multi-function force sensor presented above. One possible approach is to use a force torque sensor to replace two strain segments within the same group. FIG. 3 illustrates one example that uses a handle-mounted force torque sensor to replace the two sensing segments that are located proximally on the tool shaft, close to the handle. The strain sensor that is located distally, close to the tool tip, provides information to compensate for the force exerted close to the tool tip.

We assume that at most one contact force is applied within each sensing region. Let $F_1$ denote the force exerted in the tool portion from the tool tip to the tip strain sensor, and let $F_2$ denote the force exerted in the tool portion from tip strain sensor to the handle mounted force torque sensor. Let $l_1$ and $l_2$ denote the fixed distance from the tool tip to the tip strain sensor and the handle force torque sensor, respectively. $d_1$ denotes the distance from $F_1$ to the tip strain sensor, while $d_2$ denotes the distance from $F_2$ to the handle force torque sensor, respectively. In this example where there is only one strain sensor at the distal end of the tool shaft, close to the tip. We assume the force $F_1$ is always exerted at the tool tip, i.e. $d_1=l_1$. For the case that $d_1=l_1$, we need more than one strain sensors at the tip. Let $\epsilon t$ denote the strain measured by the tip strain sensor, and let $F_h$ and $\tau_h$ denote the force and torque measured by the handle force torque sensor. From force balance, we can write:

$$F_h = F_1 + F_2 \quad (27)$$

$$\tau_h = F_1(d_1 + \Delta l) + F_2 d_2 \quad (28)$$

$$= F_1 l_2 + F_2 d_2 \quad (29)$$

Also, we have:

$$\epsilon_t = K_{t1} F_1 \quad (30)$$

where $K_{t1}$ is a constant coefficient matrix that can be obtained through calibration. Combine (28), (29), and (30), the unknowns $F_1$, $F_2$, and $d_2$ can be easily solved:

$$F_1 = K_{t1}^\dagger \epsilon_t \quad (31)$$

$$F_2 = F_h - F_1 \quad (32)$$

$$d_2 = \frac{\tau_h - F_1 l_2}{F_2} \quad (33)$$

Figure 6:
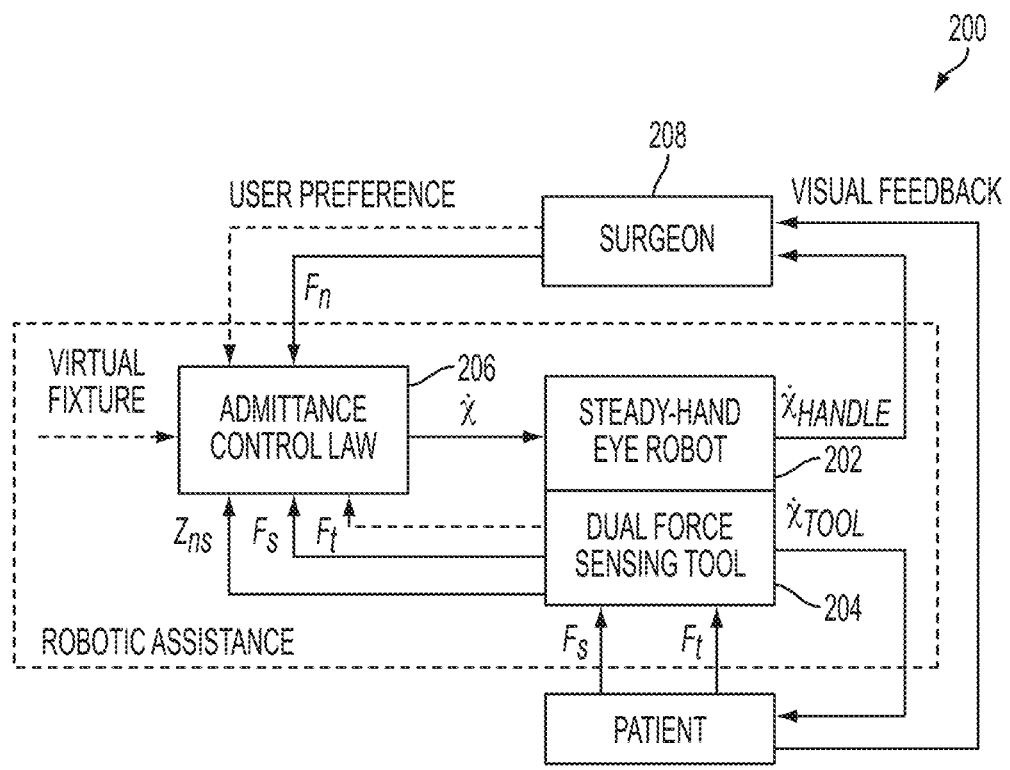
FIG. 6 is a schematic illustration of a robotic system according to an embodiment of the current invention. It also illustrates an example of a variable admittance robot control scheme according to an embodiment of the current invention. The solid lines show the signal flow in an example implementation, dashed lines show the signals that can also be incorporated into the control law.

FIG. 6 is a schematic illustration of a robotic system 200 according to an embodiment of the current invention. The robotic system 200 includes a robot 202 that has a tool connector. FIG. 6 is an example for eye surgery using a steady-hand eye robot adapted from the inventors previous work. However, the broad concepts of the current invention are not limited to only surgical robots and are not limited to only such steady hand eye robots. The robotic system 200 also includes a multi-force sensing instrument 204 attached to the tool connector of the robot 202, and a feedback system 206 configured to communicate with said multi-force sensing instrument 204 to provide at least one of feedback control of the robot 202 or feedback information to a user 208 of said robotic system 200. The multi-force sensing instrument 204 can be one or more of any of the embodiments of multi-force sensing instrument 100 described above. In some embodiments, the robotic system 200 can be a surgical robotic system; however, the general concepts of the current invention are not limited to only surgical robotic systems.

In some embodiments, the robot 202 can be a teleoperated robot. In some embodiments, the robot 202 can be a cooperatively controlled robot that performs automated functions in response to a user's actions while using said tool to at least one of modify, assist or prevent manual operations of said user's actions. In some embodiments, the robot 202 can be an RCM robot.

Detection of Patient Movement for Emergency Tool Retraction

During retinal microsurgery, the surgeon needs to monitor the unexpected patient movement, e.g., the patient sneezes, coughs, or sits up. These unexpected movements can cause collision between the ophthalmic tool and the retina, and can potentially lead to serious damage to the eye tissue. When the surgeon notices clues of such movements, the ophthalmic instruments has to be removed from the patient's eye very quickly. Previous work (X. He, D. Roppenecker, D. Gierlach, M. Balicki, K. Olds, P. Gehlbach, J. Handa, R.

Taylor, and I. Iordachita, "Toward Clinically Applicable Steady-Hand Eye Robot for Vitreoretinal Surgery," in *ASME 2012 International Mechanical Engineering Congress and Exposition*, 2012, vol. Volume 2: pp. 145-153.; M. Balicki, J. Handa, and R. Taylor, "Tool exchange interface and control algorithm for cooperative surgical robots," Patent WO2012018816 A2, 2011.) investigated the tool quick release mechanism and robot control for tool retraction.

The standard clues for eye movements are seeing the eye move in the microscope or the field of view through the lens changes, seeing "vibrations" or oscillations of the field of view, feeling resistance of the lateral forces from the instrument at the sclerotomy which gets transmitted to the instrument handle which the surgeon feels since it becomes above tactile sensation, subtle clues such as change in light reflection on the retina other structures. Both the visual and tactile cues used by the surgeon in current practice are directly associated with the sclera-to-tool interaction forces. Using the multi-function force sensing instrument, the contact force between the instrument shaft and the sclera are monitored with milli-newton sensitivity and kilohertz rate. This sensing capability can enable early detection of the unexpected patient movement. For instance, the magnitude and the first time derivative (the rate of change) of the sclera-to-tool interaction force can be used as metrics for prediction. When the sclera force magnitude crosses a given threshold, and/or exhibits high frequency oscillations (i.e., large first time derivative), the likelihood of unexpected patient motion is high. Warnings can be provided to the surgeon, e.g., using auditory/haptic feedback, to make the surgeon aware of the potential risk before the surgeon notices the standard visual and tactile clues. This can be used in both freehand and robot-assisted retinal microsurgeries. In robot-assisted procedures, the instrument motion can be used together with the force information to distinguish between the force due to the tool motion and that due to the unexpected patient movement. This can enable faster and more accurate detection of the unexpected motion, compared to the surgical scenarios in which the tool motion is not available.

Tool Retraction Using Robotic Assistance

When the unexpected patient movement is detected, the desired reaction time varies based on the speed and magnitude of movement so that the reaction time beats removing the instrument from proximity of tissue that it will potentially injure. For small movements, the surgeon simply moves the instrument away from the retina. If a patient sits up during the operation, the surgeon removes the instrument really fast. In robot-assisted procedures, similar strategies can be implemented with autonomous tool retraction methods under the surgeon's supervision.

Some embodiments of the current invention can provide the following features:

1. A surgical instrument with integrated sensing to measure contact forces and locations of these contacts on the said surgical instrument. It can provide:
   precise measurement of the location of the contact point between the surgical tool shaft and the access port with respect to the tool;
   precise measurement of the contact force between the tool shaft and the access port in 2-DOF,
   precise measurement of the tool-to-tissue force at the tool tip in 2-DOF and 3-DOF,
   and the standard surgical functionality, e.g. hook, forceps, etc.
   The sensing principle of the multi-function sensor is based on strain-gauges. In some embodiments, fiber optical sensors, i.e. fiber Bragg gratings, are used. So the surgical instrument can also be made MRI-compatible. Furthermore, other strain sensing technologies can also be used for multi-function sensing according to other embodiments of the current invention. With the same form factor, this sensor can be further extended with additional sensing segments to measure multiple contact forces and their locations.
2. A method to control a robotic manipulator using the tool forces and force locations from the surgical instrument. It can provide:
   useful feedback, such as haptic force feedback using force scaling of the force at the tool tip or that of the contact force between the tool shaft and the port
   intuitive motion constraints/guidance, such as guiding user's motion to comply with a non-static remote center-of-motion (RCM) constraint as a virtual fixture. This can provide many advantages over mechanical RCM or other mechanism, such as flexibility and safety.
   improved control of the tool tip motion with minimal tool deflection, because the side load on the tool shaft due to the contact force at the port can be minimized. This can be especially pertinent for hand-held robotic devices with small actuators, because the contact force between the port and the tool shaft can be relatively large with respect to the payload of the small actuators.
   This multi-function force sensing instrument can be incorporated with various robotic surgical systems, e.g. cooperatively controlled robot, master/slave teleoperated robot, hand-held robot, etc. We developed a control strategy for a cooperatively controlled robot to provide safe, stable surgical manipulation. Similar control can be implemented on other robotic systems and can be used for various surgical procedures, such as minimally invasive surgery, cardiac surgery, ophthalmological surgery, etc. One potential application is to provide automatic illumination assistance for ophthalmological surgery.
3. There are also other methods to present the force and force location information to the surgeon. Visual display, audio sensory substitution, and vibrotactile feedback, etc.
4. The force and force location information can be used for training and evaluation of surgical skills for residents. Some examples are:
   The ability to control the forces below a safety threshold. For example, in eye surgery, forces over 7.5 mN on the retina can potentially damage the retina. In eye surgery and minimally invasive surgery, contact forces at the port should be minimized.
   The ability to perform specific surgical tasks and surgical maneuvers, such as obey the RCM constraint at the port.

Further embodiments of the current invention include computer programs configured to perform the methods of the current invention.

The following describes some examples according to particular embodiments of the current invention. The general concepts of this invention are not limited to these particular examples.

EXAMPLES

All equation numbers in this example section refer to the equations introduced in this section, and not the equations in the previous section of this specification.

In following examples, we report a new design of a dual force sensing instrument according to an embodiment of the current invention that can sense not only the sclera force in transverse directions, but also the location of the sclera contact point on the tool shaft. This new dual force sensing instrument enables a variable admittance robot control to provide an intuitive robot behavior. By varying the robot admittance, the robot behavior can continuously transit from an adaptive virtual fixture mode that enforces RCM and adapts to the current location of the sclerotomy site, to a force scaling mode that provides scaled feedback of the sclera force as well as the ability to reposition the eye. Experiments are conducted to calibrate the new dual force sensing instrument, to calibrate the tool tip position with respect to the robot, and to evaluate the force sensor as well as the control algorithm. Results show the potential to increase safety, as well as to enhance the usability and capability of the robotic assistant system.

Dual Force Sensing Instrument

Design: Some embodiments of the current invention can build on the previous dual force sensing instrument 36. A major assumption for this example is that forces are only exerted at no more than two locations: the tool tip and the sclera contact point on the tool shaft. The tool shaft is made of a stainless steel wire with diameter of 0.5 mm, same as the 25 Ga ophthalmic instrument. The tool shaft is machined to cut three longitudinal channels with V-shape sections. One optical fiber with three fiber Bragg grating (FBG) sensors (Technica S.A., Beijing, China) is embedded into each channel in the tool shaft. Each FBG sensor is 3 mm long. The tool dimension, as well as the specifications of the FBG sensors are shown in FIGS. 2A-2D.

The new dual force sensing instrument includes nine FBG sensors in total, arranged into three segments of the tool shaft. The three FBG sensors in the same tool shaft segment are 120° apart, and provide strain measurements at that segment of the tool shaft. The first FBG sensing segment, FBG-I, typically remains inside the eye. It is used to measure the transverse force exerted between the tool tip and the eye tissue, because the sclera contact force does not generate strain at the tool tip. FBG-II and FBG-III sensing segments are at least 30 mm proximal from the tool tip, greater than the average diameter of human eye (25 mm). They are dedicated to measure the transverse force exerted at the sclerotomy, and the location of the sclerotomy with respect to the tool. The axial force component at the sclerotomy is mainly due to friction, thus is correlated to the transverse force, i.e. normal force. Axial force sensing at the tip is not included in this prototype, but is possible as shown in our other work 33. The total length of the tool shaft is 45 mm. The data acquisition unit is the sm130-700 optical sensing interrogator from Micron Optics (Atlanta, Ga.) with a refresh rate of 2 kHz and a spectrum range from 1525 nm to 1565 nm.

Algorithm to Calculate Forces and Sclerotomy Location

The algorithm to calculate the sclera and tip forces is based on the previous methods presented by Iordachita et al. 30 and He et al. 36. The wavelength shift common mode of the FBG sensors from the same sensing segment represents the strain attributed to axial force and temperature change. The differential mode, termed sensor reading, is defined as follows:

$$\Delta s_{jk} = \Delta \lambda_{jk} - \frac{1}{3}\sum_{k=1}^{3} \Delta \lambda_{jk} \tag{1}$$

where $\Delta s_{jk}$ and $\Delta \lambda_{jk}$ denotes respectively the sensor reading and the wavelength shift of FBG sensor kin sensing segment j, with j=I, II, and III, and k=1, 2, and 3.

With the assumption that tool-to-tissue interaction forces are always exerted at the tool tip, the sensor readings of FBG-I are linearly dependent on the transverse force at the tool tip:

$$\Delta S_I = K_{It} F_t \tag{2}$$

where $\Delta S_I = [\Delta s_{I1}, \Delta s_{I2}, \Delta s_{I3}]$ denotes the sensor readings of FBG-I, $F_t = [F_{tx}, F_{ty}]^T$ denotes the transverse force exerted at the tool tip, and $K_{It}$ is a 3×2 matrix with constant coefficients.

The location where the sclera contact force is exerted on the tool shaft depends on the tool insertion depth inside the eye. Together with the sclera contact force, it contributes to the strain generated at FBG-II and FBG-III. In addition, the FBG sensors also respond to tip force, therefore:

$$\Delta S_j = K_{jt} F_t + K_{js} M_j \Delta S_j \tag{3}$$
$$= K_{jt} F_t + K_{js} M_j$$
$$= K_{jt} F_t + K_{js} F_s d_j \tag{4}$$

where $\Delta S_j = [\Delta s_{j1}, \Delta s_{j2}, \Delta s_{j3}]^T$ denotes the sensor readings of FBG-j, $F_s = [F_{sx}, F_{sy}]^T$ denotes the transverse force exerted at the sclerotomy, $d_j$ denotes the distance from the sclerotomy to FBG-j along the tool shaft, $M_j = [M_{jx}, M_{jy}]^T$ denotes the moment attributed to $F_s$ at FBG-j, $K_{jt}$ and $K_{js}$ are both 3×2 constant coefficients matrices, j=II and III. As shown in FIG. 2, the distance $\Delta l$ between FBG-II and FBG-III is constant and is always the difference between $d_{II}$ and $d_{III}$, which equals to the difference between $l_{II}$ and $l_{III}$:

$$\Delta l = l_{III} - l_{II} = d_{III} - d_{II} \tag{5}$$

The coefficient matrices $K_{jt}$ (j=I, II, and III) and $K_{js}$ (j=II and III), as well as the distance $\Delta l$ between FBG-II and FBG-III are obtained through the tool calibration described in more detail below.

The tip force can be calculated using the pseudo-inverse of the coefficient matrix:

$$F_t = K_{It}^\dagger \Delta S_I \tag{6}$$

where $(\bullet)^\dagger$ denotes the pseudo-inverse operator.

The moments attributed to the sclera contact forces at FBG-j (j=II and III) can be calculated using (3) and (6):

$$M_j = K_{js}^\dagger (\Delta S_j - K_{jt} K_{It}^\dagger \Delta S_I) \tag{7}$$

The sclera contact force can be solved from the difference in moments $M_{II}$ and $M_{III}$:

$$F_s = \frac{M_{III} - M_{II}}{\Delta l} \tag{8}$$

The distance from the sclerotomy to the FBG-j can be obtained from the magnitude ratio between the moment and the force:

$$d_j = \frac{\|M_j\|}{\|F_s\|} \tag{9}$$

where $\|\bullet\|$ denotes the vector 2-norm.

This method can calculate transverse forces exerted at the tool tip and at the sclerotomy, as well as the location of the sclerotomy with respect to the tool. However, if the magnitude of the sclera contact force is small, the location of the sclerotomy calculated using (9) can be subject to large error. Therefore, the sclerotomy location is updated with the help of a deadband on the sclera force magnitude. Only when the sclera force magnitude exceeds a given threshold (e.g. 5 mN), the sclerotomy location will be updated using (9), otherwise the previous value of $d_j$ will be used.

Variable Admittance Robot Control

A variable admittance robot control scheme is devised from previous force scaling and admittance velocity control 3537. In addition to the surgeon's force input at the tool handle (robot end-effector), it utilizes the new sensing capabilities enabled by the dual force sensing instrument, to provide a robot behavior that is transparent and intuitive to the surgeon. This robot behavior enables useful feedback and virtual fixtures to increase precision and safety to interact with the patient and the environment. FIG. 6 illustrates the variable admittance control scheme.

Constant Admittance Control with Force Scaling

The previous admittance velocity control is:

$$\dot{x}_{hh} = \alpha F_{hh} \quad (10)$$

$$\dot{x}_{wh} = Ad_{g_{wh}} \dot{x}_{hh} \quad (11)$$

where $\dot{x}_{wh}$ and $\dot{x}_{hh}$ are the desired robot handle velocity in the robot handle frame and that in the world Cartesian frame, respectively, $F_{hh}$ denotes user's force input measured in the robot handle frame, and $\alpha$ is a constant scalar as the admittance gain, and $Ad_{g_{wh}}$ is the adjoint transformation associated with coordinate frame transformation $g_{wh}$ 38. If we write $$g_{wh} = \begin{bmatrix} R_{wh} & p_{wh} \\ 0 & 1 \end{bmatrix},$$

where $R_{wh}$ and $p_{wh}$ denote the rotation and translation of $g_{wh}$ from the local robot handle frame to the world Cartesian frame, then:

$$Ad_{g_{wh}} = \begin{bmatrix} R_{wh} & \hat{p}_{wh} R_{wh} \\ 0 & R_{wh} \end{bmatrix} \quad (12)$$

where $\hat{p}_{wh}$ denotes the skew symmetric matrix that is associated with the vector $p_{wh}$.

We modify (10) using force scaling 3537 to incorporate sclera force feedback:

$$\dot{x}_{hh} = \alpha(F_{hh} + \gamma F_{hs}) \quad (13)$$

where $\gamma$ is a force scaling factor, and $F_{hs}$ is the sclera force resolved at the robot handle with the following adjoint transformation:

$$F_{hs} = Ad_{g_{hs}}^T F_{ss} \quad (14)$$

where $F_{ss}$ denotes the sclera force measured in the sclera frame which is located at the sclerotomy and has the same orientation as the handle frame. Let $$g_{hs} = \begin{bmatrix} R_{hs} & p_{hs} \\ 0 & 1 \end{bmatrix},$$

denote the coordinate frame transformation from sclera frame to handle frame, then:

$$Ad_{g_{hs}}^T = \begin{bmatrix} R_{hs}^T & 0 \\ -R_{hs}^T \hat{p}_{hs} & R_{hs}^T \end{bmatrix} \quad (15)$$

where $(\cdot)^T$ denotes the matrix transpose. The sclerotomy is not a static point during retinal microsurgery. Therefore, $g_{hs}$ is time-varying. We assume that the tool shaft bending due to sclera force remains in a small range, then $R_{hs} \approx 1$, $p_{hs} \approx [0, 0, z_{hs}]^T$ and $z_{hs}$ can be updated by the dual force sensing instrument.

Variable Admittance Control

The admittance in the previous control law is isotropic. Virtual fixtures can be rendered by commanding anisotropic admittance. We introduce diagonal admittance matrices into (13) and rewrite it in the sclera frame:

$$\dot{x}_{ss} = \alpha(A_{sh} F_{sh} + \gamma A_{ss} F_{ss}) \quad (16)$$

where $\dot{x}_{ss}$ is the desired velocity of where the robot/tool contact the sclerotomy in the sclera, $F_{sh}$ and $F_{ss}$ are the handle input force and sclera contact force resolved in the sclera frame, respectively, $\gamma$ denotes the constant scalar as the force scaling factor, $\alpha$ denotes the constant scalar as the admittance gain, and $A_{sh}$ and $A_{ss}$ are the diagonal admittance matrices associated with the handle input force and sclera contact force in the sclera frame, respectively. If $A_{sh} = A_{ss} = 1$, (16) reduces to (13) as force scaling of the sclera force.

A virtual RCM can be realized by setting $A_{sh} = \text{diag}([0, 0, 1, 1, 1, 1]^T)$ and $A_{ss} = 1$. The handle input force $F_{sh}$ is resolved in the sclera frame. The admittance matrix $A_{sh}$ removes the transverse force components that can lead to undesired lateral motion, and preserves the 4-DOF motion that is allowed by the RCM constraints. In addition, the sclera force feedback is to servo the sclera contact force toward zero. This strengthens the virtual RCM with robustness against eye motion attributed other instrument and patient movement.

Figure 7:
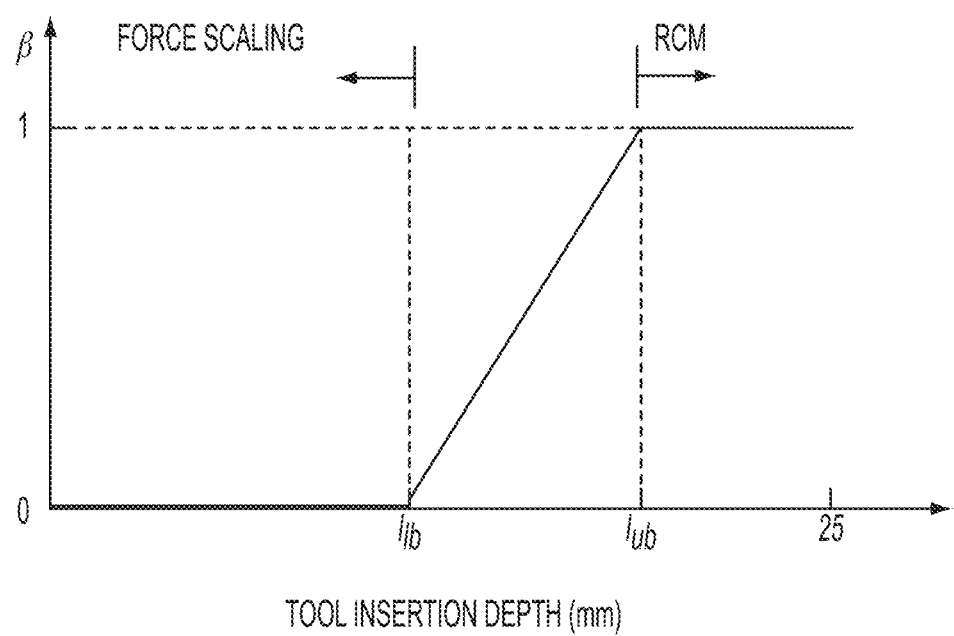
FIG. 7 shows how admittance varies along with the insertion depth for an example according to an embodiment of the current invention. The section between $l_{lb}$ and $l_{ub}$ is the transition between pure force scaling of the sclera force and pure RCM.

When the surgeon is performing ERM peeling, the tool tip is close to the retina, and an RCM is desired to minimize the motion of the eye and the target membrane. When the surgeon needs to reposition the eye to adjust view, the tool is kept away from the retina to avoid collision. Therefore, the measured insertion depth of the tool can be used to adjust the robot admittance to provide the appropriate robot behavior. For example, we can define:

$$A_{sh} = \text{diag}([1-\beta, 1-\beta, 1, 1, 1, 1]^T) \quad (17)$$

$$A_{ss} = \text{diag}([1+\beta, 1+\beta, 1, 1, 1, 1]^T) \quad (18)$$

where $\beta \in [0, 1]$ varies along with the tool insertion depth as shown in FIG. 7. When the insertion depth is smaller than the given lower bound $l_{lb}$, $\beta=0$ and $A_{sh} = A_{ss} = 1$. We have the force scaling control mode that provides the freedom to reposition the eye with scaled sclera force feedback. When the insertion depth is larger than the given upper bound $l_{ub}$, $\beta=1$ and it switches to virtual RCM with doubled gain for minimizing the transverse forces at the sclerotomy. Alternatively, the value of $\beta$ can be controlled by the human operator (e.g. using a foot pedal) to select the preferred operating mode.

Experiments and Results

Calibration of the Dual Force Sensing Instrument

An automated calibration system 33 is used to carry out the calibration. Transverse forces are applied at different locations on the tool. The wavelength shifts of the FBG sensors, applied forces, and the location on the tool where the forces are applied are measured and recorded.

Calibration for Tip Force

Figures 8A, 8B, 8C, 8D:
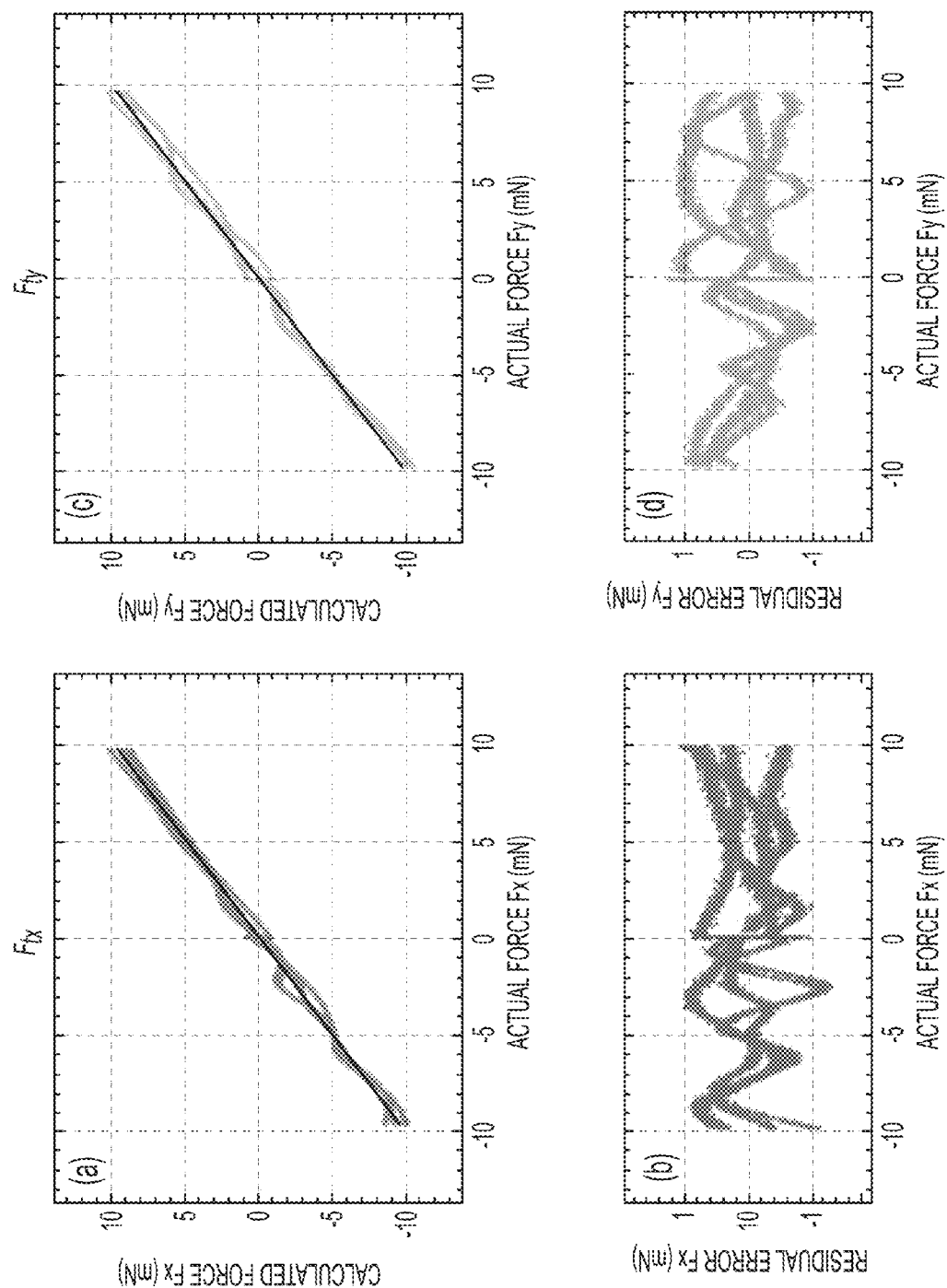
FIGS. 8A-8D provide results of tool tip force calibration for an example according to an embodiment of the current invention. The calculated tool tip force along X-axis $F_{tx}$ versus the actual value (a), its residual error (b). The calculated tool tip force along Y-axis $F_{ty}$ versus the actual value (c), and its residual error (d).

The calibration for tip force is the same as for our previous dual force sensing tool 36. Transverse forces up to 10 mN are applied along X- and Y-axes. The coefficient matrices $K_{jt}$, j=1, 2, and 3, are obtained as least square solution of (2) and (3) with $M_j$=0. FIGS. 8A-8D illustrate the calibration results for the tip forces. FIGS. 8A and 8C show the forces calculated using (6) versus the actual forces. The 45° straight line through the origin represents the ideal results. FIGS. 8B and 8D show the residual error versus the actual forces. The root mean square (RMS) errors are 0.35 mN for $F_{tx}$ and 0.53 mN for $F_{ty}$, respectively.

Calibration for Sclera Contact Force and Location

Transverse forces are applied at 16 locations on the tool shaft, from 10 mm to 25 mm proximal from the tool tip with 1 mm intervals, shown as d in FIG. 2C. The force magnitude ranges from 25 mN at 10 mm from the tool tip, to 100 mN at 25 mm from the tool tip. Because the optical fibers are manually aligned and embedded into the tool shaft, the accurate "center" locations of FBG-II and FBG-III, i.e. $l_{II}$ and $l_{III}$ in FIG. 2C, are not known. There is no force applied at the tool tip, hence (4) reduces to:

$$\Delta S_j = K_{js} F_s d_j \qquad (19)$$

$$= K_{js} F_s (l_j - d_s) \qquad (20)$$

where $d_j = l_j - d_s$ with j=II and III.

The calibration goal is to find the constant $K_{js}$ and $l_j$. Because they are not linearly independent, an optimization problem is constructed to find the best fit:

$$\operatorname{argmin}_{l_j} \|\Delta S_j - \overline{K}_{js} F_s (l_j - d_s)\| \qquad (21)$$

$$\text{s.t. } \overline{K}_{js} = \Delta S_j (F_s (l_j - d_s))^\dagger \qquad (22)$$

$$25 \le l_j \le 50 \qquad (23)$$

Figure 9A:
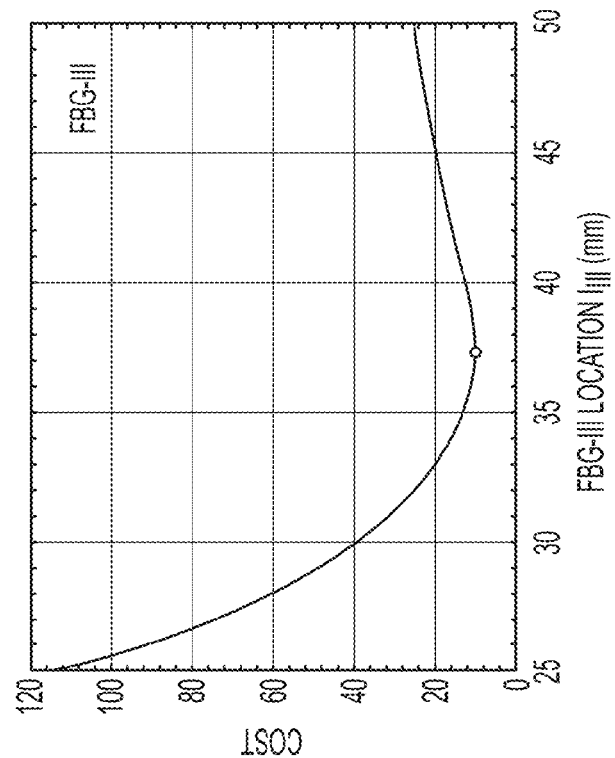
FIGS. 9A and 9B show results of the optimization problem. The optimization cost for FBG-II versus $l_{II}$ (a) and the optimization cost for FBG-III versus $l_{III}$ (b). The red dots indicate the minimum cost where $l^*_{II}$=31.3 mm and $l^*_{III}$=37.2 mm.
Figure 9B:
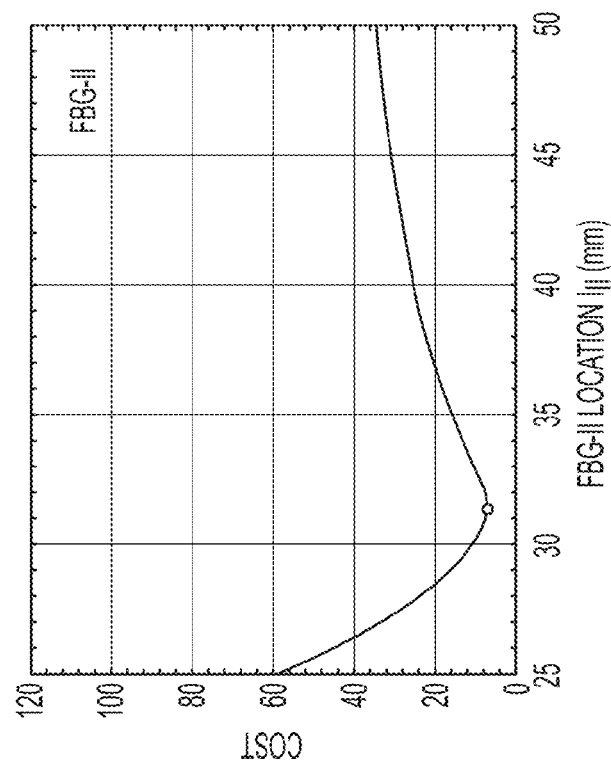
Figures 10A, 10B, 10C, 10D:
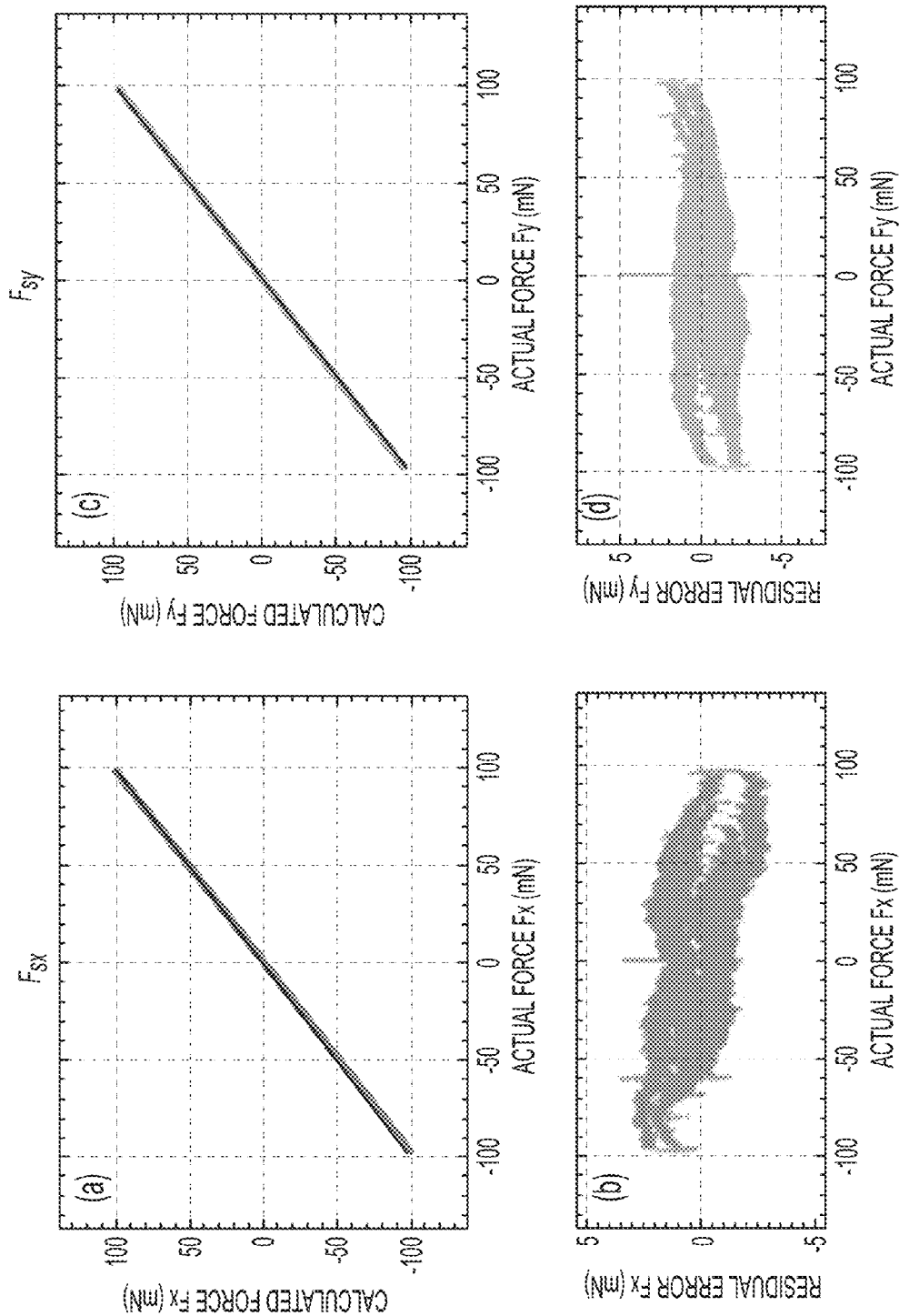
FIG. 10A-10D show results of sclera force calibration. The calculated sclera force along X-axis Fsx versus the actual value (a), its residual error (b). The calculated sclera force along Y-axis Fsy versus the actual value (c), and its residual error (d).

The optimum $l^*_j \in [25, 50]$ minimizes the cost function, i.e. the 2-norm of the residual error of the sensor reading of FBG-j. FIGS. 9A and 9B illustrate the optimization results. $l^*_{II}$ and $l^*_{III}$ are 31.3 mm and 37.2 mm, respectively. The difference between FBG-II and FBG-III $\Delta l = l^*_{III} - l^*_{II} = 5.9$ mm, is consistent with the nominal value of 6 mm in a single fiber.

Figure 11B:
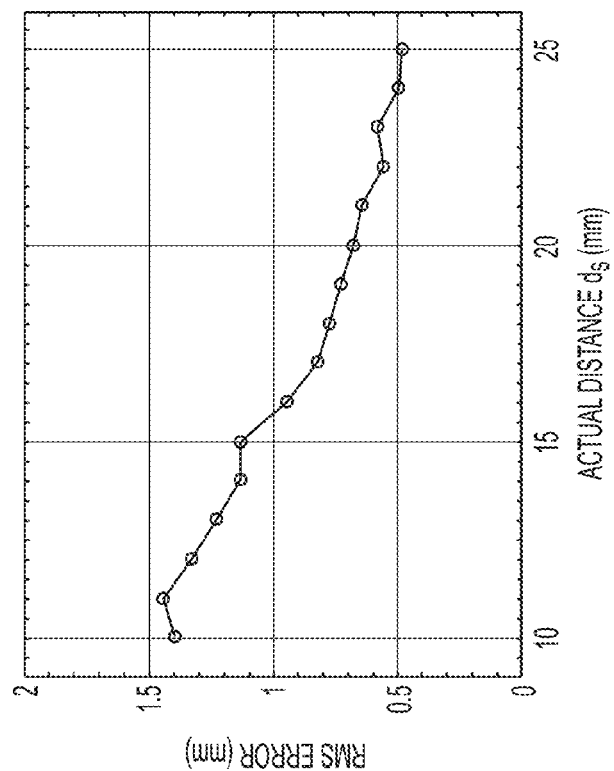
FIGS. 11A and 11B show results of sclerotomy location calibration. The calculated distance from the tool tip to sclerotomy ds versus the actual value (a), the RMS error at each calibrated location versus the actual distance (b). The further the scleratomy is located from the tool tip, i.e., the closer it is with respect to FBG-II and FBG-III, the smaller is the RMS error. Data points with forces smaller than 5 mN in magnitude is not included to reduce noise, as discussed in Section II-B.
Figure 11A:
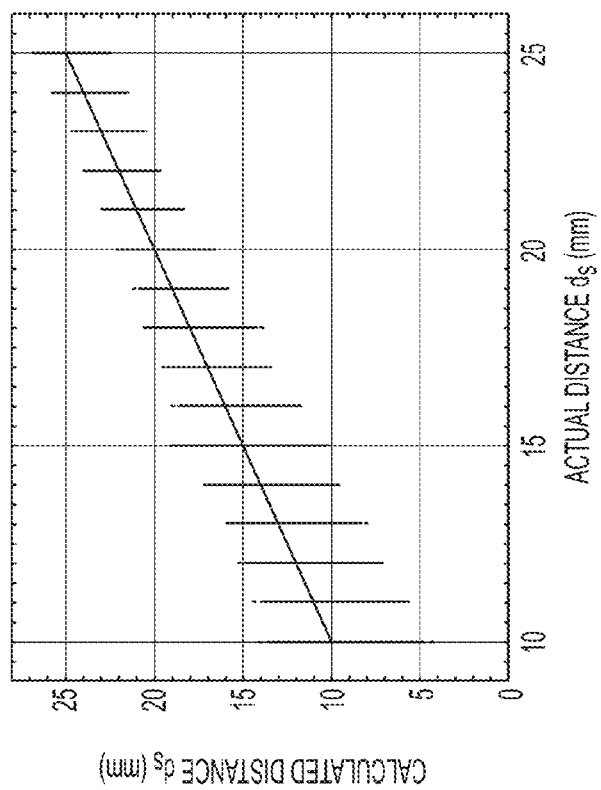

The coefficient matrix $K_{js}$ is calculated using (22) with $l^*_j$. Calibration results demonstrate sufficient accuracy, as shown in FIGS. 10A-10D. The RMS errors are 0.82 mN for $F_{sx}$ and 1.00 mN for $F_{sy}$. The location of the sclerotomy is estimated using forces larger than 5 mN in magnitude. FIGS. 11A and 11B illustrate the estimated sclerotomy location with respect to the tool tip versus the actual value, and the estimation RMS error at each calibrated location. The further the sclerotomy is located from the tip, the closer it is to FBG-II and FBG-III, and the more accurate is the location estimation. As shown in next section, low-pass filtering can further reduce the sensing noise and smooth the estimation.

Figure 12B:
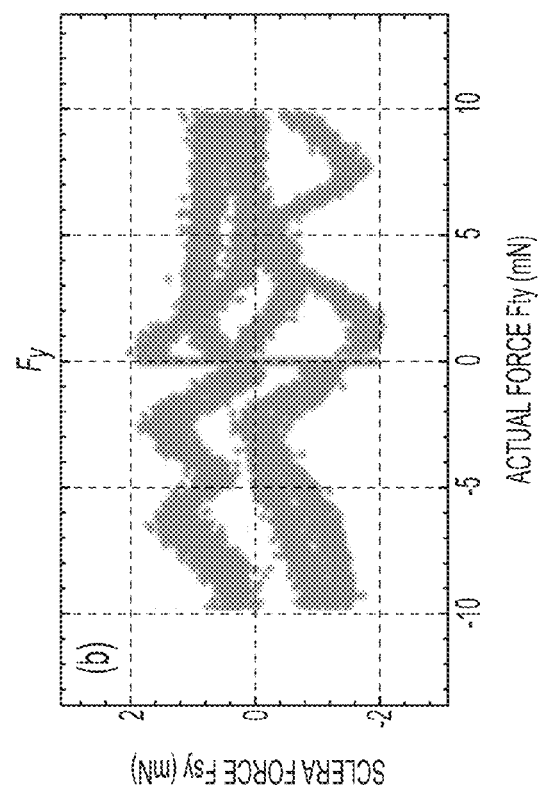
FIGS. 12A and 12B show sclera force estimation error due to tool tip force. The calculated sclera force along X-axis $F_{sx}$ versus the applied tool tip force along X-axis $F_{tx}$ (a), and the calculated sclera force along Y-axis $F_{sy}$ versus the applied tool tip force along Y-axis $F_{ty}$ (b).
Figure 12A:
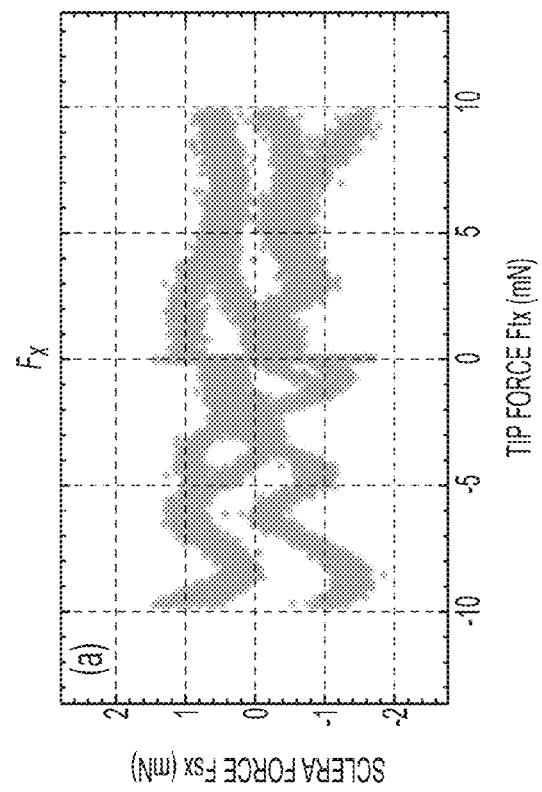
Figures 13A, 13B, 13C, 13D:
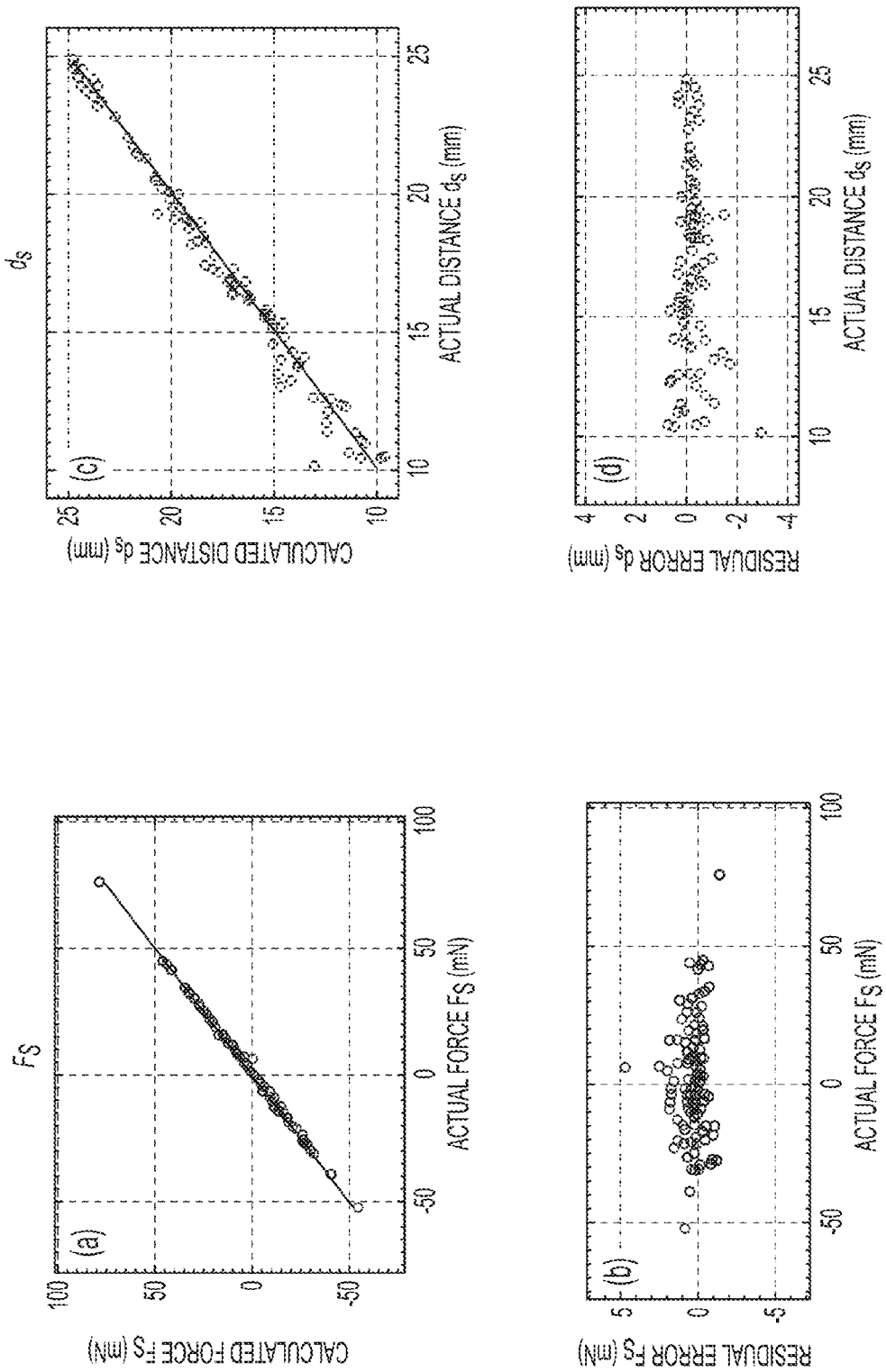
FIGS. 13A-13D show results of validation experiment for sclera contact force. The calculated sclera force versus the actual value (a), the residual error of force calculation (b). The calculated distance from the tool tip to sclerotomy ds versus the actual value (c), and its residual error (d).

Using the sclera calibration results, we examine the tip force cancellation from FBG-II and FBG-III. The sensor readings of FBG-II and FBG-III from calibration with only tip forces are plugged into (7) and (8) to calculate the sclera force estimation error due to tip force. As shown in FIGS. 12A and 12B, the sclera force errors are not dependent on the tip force magnitude, and are possibly due to the system noise. The RMS errors are 0.62 mN for $F_{sx}$ and 0.74 mN for $F_{sy}$, with tip forces up to 10 mN.

Validation Experiment for Sclera Contact Force

A validation experiment is carried out using the automated calibration system to test the results obtained from calibration for sclera force and location. The direction and the magnitude of the transverse forces, as well as the location on the tool shaft where the force is applied are generated randomly within the calibrated range. A moving average filter with a window size of 100 samples is applied on the location estimation of sclerotomy. FIGS. 13A-13D illustrate the results of the validation experiment. The RMS errors of $F_{sx}$ and $F_{sy}$ estimations are 0.56 mN and 1.08 mN respectively. The RMS error of the sclerotomy location estimation is 0.57 mm, comparable to the lowest error obtained in the calibration at 25 mm from the tool tip.

Tool to Robot Calibration

Figure 14B:
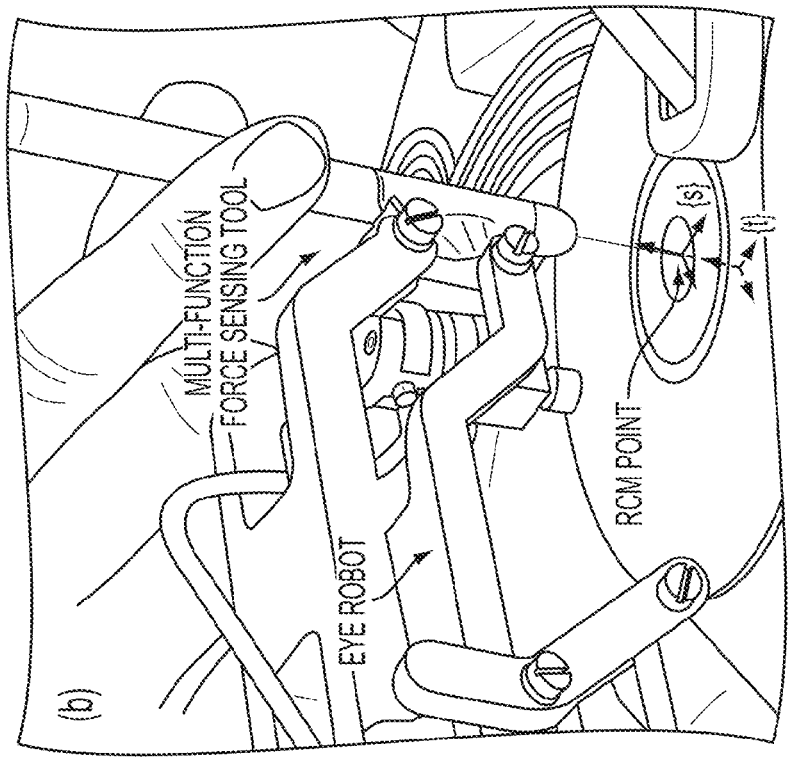
FIGS. 14A and 14B show setup of the pseudo pivot calibration (a) and the close-up with coordinate frames robot handle {h}, sclera {s}, and tool tip {t} (b). Tool tip frame {t} is underneath the CD, shown with dashed arrows.
Figure 14A:
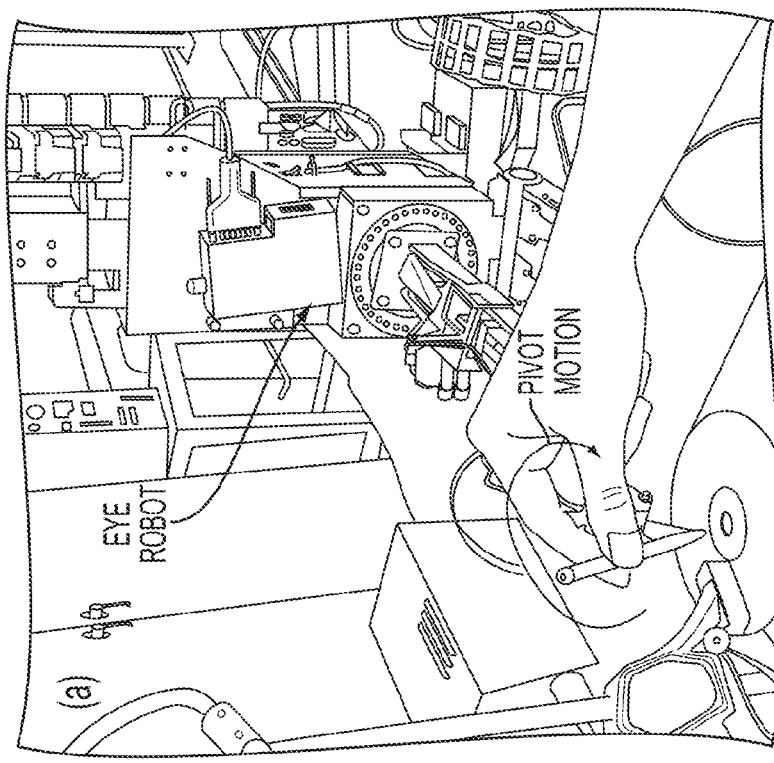

Incorporating dual force sensing capability into the robot control requires an accurate coordinate transformation from the local tool frame to the robot tool holder frame. It is reasonable to assume the tool and the tool holder are coaxial. The X- and Y-axes of the tool and the robot tool holder are manually aligned. The Z-offset $z_{rt}$ from the robot tool holder to the tool tip is about −40 mm measured with a caliper. A traditional pivot calibration is not practical, because the tool shaft is not rigid. We use variable admittance control to enforce the RCM constraint, and to perform a pseudo pivot calibration. FIGS. 14A and 14B illustrate the experiment setup. A piece of 0.25 mm thick, stiff paper is taped to a CD clamped to a stable platform. A 0.7 mm hole is punctured in the center of the paper that is exposed through the center hole of the CD. The dual force sensing tool is inserted into the hole and pivoted with the RCM constraint by the variable admittance control, as shown in FIG. 14A.

The sclera location estimations $d_s$ from the dual force sensing tool and the frame transformations from the world Cartesian frame to the robot tool holder frame $g_{wr}$ are used to find the tool tip offset from the tool holder. Let $g_{rs}$ denote the frame transformation from the "sclera" frame located at the RCM point to the robot tool holder frame. Because we assume the orientation of "sclera" RCM frame is aligned with that of the robot tool holder frame:

$$g_{rs} = \begin{bmatrix} R_{rs} & p_{rs} \\ 0 & 1 \end{bmatrix} \qquad (24)$$

where $R_{rs}=I$, $p_{rs}=[0, 0, z_{rt}+d_s]^T$, and $z_{rt}$ is the Z-position of the tool tip in the robot tool holder frame. The RCM point $p_{ws}$ can be considered as a static point in the world Cartesian frame. Ideally, all $p_{ws}$ computed from the kinematics should converge to one point. Therefore, an optimization problem that finds the $z^*_{rt}$ to minimize the standard deviation of all $p_{ws}$:

$$\operatorname{argmin}_{z_{rt}} \|\sigma(P_{ws})\| \qquad (25)$$

$$\text{s.t. } P_{ws} = [\, p_{ws1} \; \ldots \; p_{wsn} \,]^T \qquad (26)$$

-continued $$\begin{bmatrix} p_{wsk} \\ 1 \end{bmatrix} = g_{wrk} \begin{bmatrix} p_{rsk} \\ 1 \end{bmatrix}, k = 1, \ldots, n \quad (27)$$

$$-45 \le z_{rt} \le -35 \quad (28)$$

FIG. 15A shows the optimization results, $z^*_{rt}=39.4$ mm. The corresponding trajectories of the RCM point and the tool tip are shown in FIG. 15B. The standard deviation of the computed RCM positions is 0.38 mm, 0.34 mm and 0.74 mm in the X-, Y-, and Z-direction, respectively. This demonstrates the capability of adaptive RCM constraints enabled by the variable admittance control.

Tracing a Retina Vein in an Eye Phantom

Figure 16:
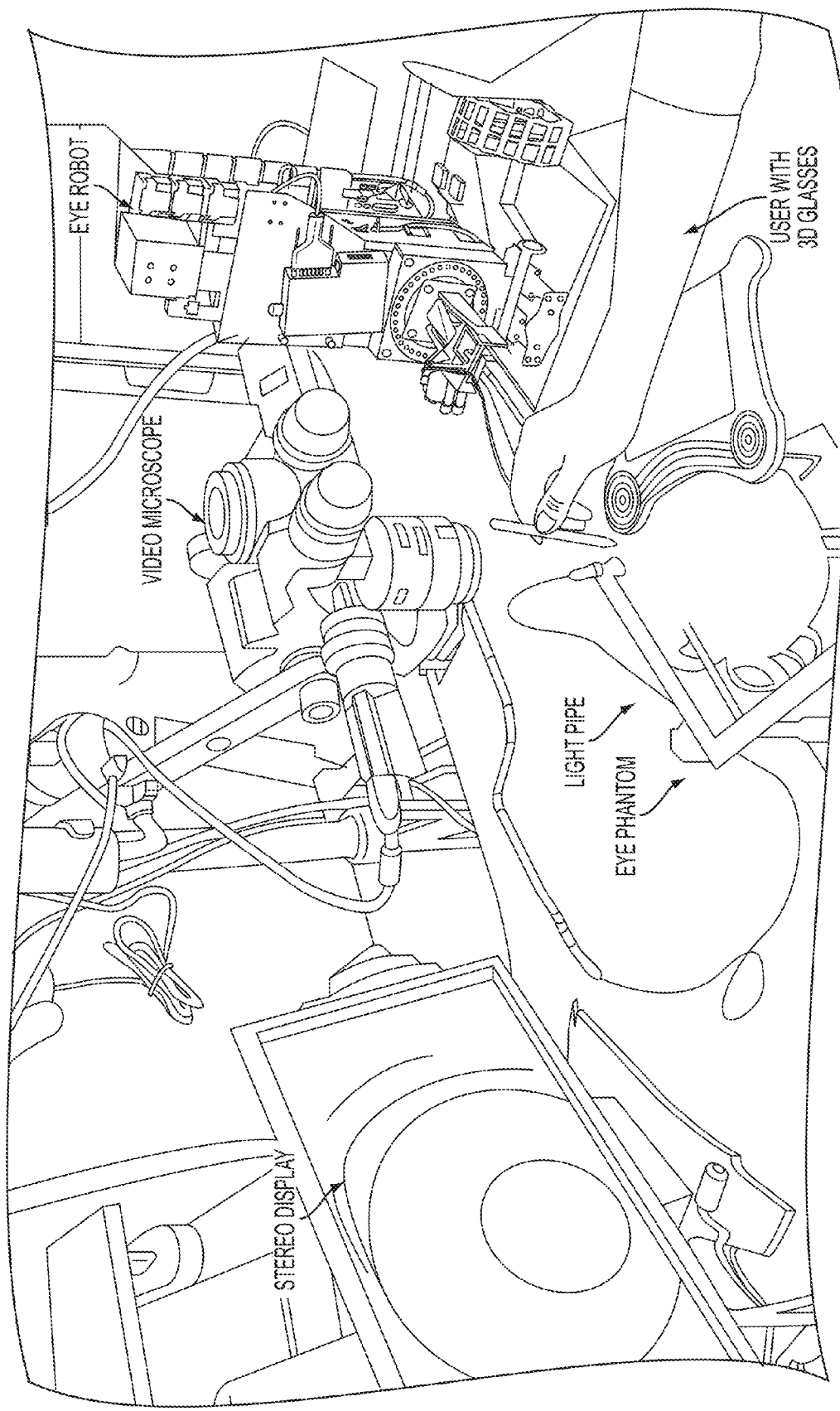
FIG. 16 shows the setup of the retina vein tracing experiment with robotic assistance.

We further assess the performance of the robot control using an eye phantom, as shown in FIG. 16. The tool is inserted through a 23 Ga trocar on the eye and is used to trace a vein on the retina. A stereo video microscope with a 3D display is used for visualization.

Figures 17A, 17B:
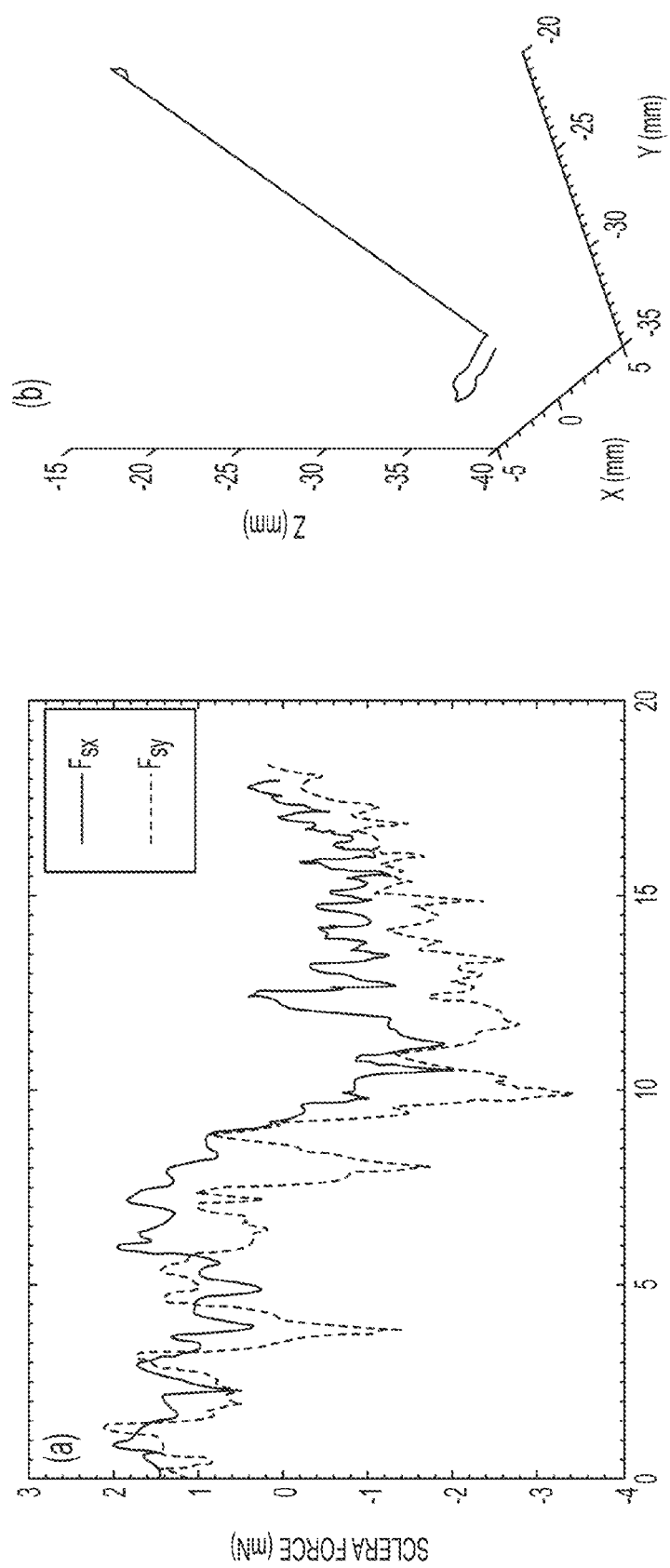
FIGS. 17A and 17B show sclera force of one retina vein tracing trial (a). The corresponding trajectories of the scleratomy point (top) and the tool tip (bottom) (b). The black straight line shows the end position of the tool shaft.

The task is to make a round trip above a retina vein branch that is about 3 mm long. Five trials are conducted with the variable admittance control. FIGS. 17A and 17B illustrate the recorded sclera forces, as well as the trajectory of the sclerotomy point and the tool tip of one of the trials. The maximum sclera force magnitude is 3.44±0.21 mN, The sclerotomy position is calculated using the tool-to-robot transformation obtained above. The standard deviation of the sclerotomy position is 0.13+0.03 mm, 0.17±0.06 mm, and 0.38±0.06 mm for X-, Y-, and Z-direction, The experiment results show the RCM behavior with the variable admittance control is precise and repeatable, minimizing both force and motion of the sclerotomy.

The same task is also attempted with the standard cooperative control without sclera force feedback. The user cannot feel the sclera force, and can only rely on the visual feedback provided by the 3D display. The severe tool deflection due to large sclera forces (over 50 mN) and the inverted motion due to RCM make it very difficult to control the tool tip motion. No successful trial was completed. In contrast, the variable admittance control enables a fulcrum at the sclerotomy, the user pivots naturally about it with precise control of the tool tip motion.

DISCUSSION AND CONCLUSION

Krupa et al. 39 used force control with the help of a force sensor mounted on the robot end-effector to implement an adaptive RCM behavior. However, it was assumed that there was no transverse forces exerted at the instrument tip, therefore the transverse forces measured outside the patient at the robot end-effector was the contact force exerted between the instrument shaft and the trocar. This assumption is not necessarily valid in MIS. The dual force sensing instrument can provide sufficiently accurate, independent measurements of the tool tip force and the sclera contact force, as well as the location of the sclerotomy. Its design can also be applied to surgical instruments for MIS, to provide additional useful information to improve the surgical robot control, Both impedance and admittance type robots can utilize this sensor to provide safe interaction with the environment. This can be especially pertinent for bilateral cooperative manipulation and telesurgery.

The variable admittance control takes the sensing advantage from the dual force sensing instrument. It reflects the natural physical interaction between the tool and the environment. It can adapt to the current RCM point without the assumption that the RCM point is static. Mechanical RCM does not provide the flexibility to vary the RCM point, while software virtual RCM that uses geometric constraints can incorporate the dual force sensing instrument to update the current RCM point. The variable admittance control law can also be incorporated with other virtual fixture methods, such as the constrained optimization framework 2223. Ultimately, it should provide a transparent and intuitive interface that can incorporate useful feedback and natural motion guidance.

We have presented a novel multi-function force sensing instrument designed for vitreoretinal surgery procedures that measures not only the forces at the instrument tip, but also the sclera contact position and interaction force on shaft of the instrument. A variable admittance robot control method was developed that incorporates this information to provide a transparent and intuitive robot behavior that can minimize eye motion while enabling tool manipulation inside the eye, as well as provide useful sclera force feedback to assist to reposition the eye. This system can potentially provide safe, stable micromanipulation that can improve the outcome of the retinal microsurgery.

REFERENCES

1. J. R. Wilkins, C. A. Puliafito, M. R. Hee, J. S. Duker, E. Reichel, J. G. Coker, J. S. Schuman, E. A. Swanson, and J. G. Fujimoto, "Characterization of epiretinal membranes using optical coherence tomography.," *Ophthalmology*, vol. 103, no. 12. pp. 2142-2151, 1996.
2. M. Patkin, "Ergonomics applied to the practice of microsurgery.," *The Australian and New Zealand Journal of Surgery*, vol. 47, no. 3, pp. 320-329, 1977.
3. P. Gupta, P. Jensen, and E. de Juan, "Surgical forces and tactile perception during retinal microsurgery," in *MICCAI,* 1999, vol. 1679, pp. 1218-1225.
4. R. H. Taylor, J. Funda, D. D. Grossman, J. P. Karidis, and D. A. LaRose, "Remote center-of-motion robot for surgery," U.S. Pat. No. 5,397,323, Mar. 14, 1995.
5. J.-P. Hubschman, J. Son, B. Allen, S. D. Schwartz, and J.-L. Bourges, "Evaluation of the motion of surgical instruments during intraocular surgery," *Eye (London, England)*, vol. 25, no. 7, pp. 947-953, 2011.
6. S. Charles, H. Das, T. Ohm, C. Boswell, G. Rodriguez, R. Steele, and D. Istrate, "Dexterity-enhanced telerobotic microsurgery," in *IEEE ICRA,* 1997, pp. 5-10.
7. T. Nakano, N. Sugita, T. Ueta, Y. Tamaki, and M. Mitsuishi, "A parallel robot to assist vitreoretinal surgery," *IJCARS*, vol. 4, no. 6, pp. 517-526, 2009.
8. Y. Ida, N. Sugita, T. Ueta, Y. Tamaki, K. Tanimoto, and M. Mitsuishi, "Microsurgical robotic system for vitreoretinal surgery," *IJCARS*, vol. 7, no. 1, pp. 27-34, 2012.
9. W. Wei, R. Goldman, and N. Simaan, "Design and theoretical evaluation of microsurgical manipulators for orbital manipulation and intraocular dexterity," in *IEEE ICRA,* 2007, pp. 10-14.
10. H. Yu, J. H. Shen, K. M. Joos, and N. Simaan, "Design, Calibration and preliminary testing of a robotic telemanipulator for OCT guided retinal surgery," in *IEEE ICRA,* 2013, pp. 225-231.
11. R. A. Maclachlan, B. C. Becker, J. C. Tabar, G. W. Podnar, L. A. Lobes, and C. N. Riviere, "Micron: an actively stabilized handheld tool for microsurgery," *IEEE Transactions on Robotics*, vol. 28, no. 1, pp. 195-212, 2012,
12. C. Song, D. Y. Park, P. L. Gehlbach, S. J. Park, and J. U. Kang, "Fiber-optic OCT sensor guided 'SMART' micro-forceps for microsurgery," *Biomedical Optics Express*, vol. 4, no. 7, pp. 1045-1050, 2013.
13. M. P. Kummer, S. S. Member, J. J. Abbott, B, E. Kratochvil, R. Borer, A. Sengul, B. J. Nelson, and S. S. Member, "OctoMag: an electromagnetic system for 5-DOF wireless micromanipulation," *IEEE Transactions on Robotics*, vol. 26, no. 6, pp. 1006-1017, 2010.
14. R. Taylor, P. Jensen, L. Whitcomb, A. Barnes, R. Kumar, D. Stoianovici, P. Gupta, Z. Wang, E. DeJuan, and L. Kavoussi, "A Steady-Hand Robotic System for Microsurgical Augmentation," *The IJRR*, vol. 18, no. 12, pp. 1201-1210, 1999.
15. B. Mitchell, J. Koo, I. Iordachita, P. Kazanzides, A. Kapoor, J. Handa, G. Hager, and R. Taylor, "Development and application of a new steady-hand manipulator for retinal surgery," in *IEEE ICRA*, 2007, pp. 623-629.
16. A. Uneri, M. A. Balicki, J. Handa, P. Gehlbach, R. H. Taylor, and I. Iordachita, "New Steady-Hand Eye Robot with micro-force sensing for vitreoretinal surgery," in *IEEE BioRob*, 2010, pp. 814-819.
17. X. He, D. Roppenecker, D. Gierlach, M. Balicki, K. Olds, P. Gehlbach, J. Handa, R. Taylor, and I. Iordachita, "Toward clinically applicable Steady-Hand Eye Robot for vitreoretinal surgery," in *ASME IMECE*, 2012, IMECE2012-88384.
18. L. B. Rosenberg, "Virtual fixtures: Perceptual tools for telerobotic manipulation," in *IEEE Virtual Reality Annual International Symposium*, 1993, pp. 76-82.
19. J. J. Abbott and A. M. Okamura, "Virtual fixture architectures for telemanipulation," in *IEEE ICRA*, 2003, pp. 2798-2805.
20. A. Bettini, P. Marayong, S. Lang, A. M. Okamura, and G. D. Hager, "Vision-assisted control for manipulation using virtual fixtures," *IEEE Transactions on Robotics*, vol. 20, no. 6, pp. 953-966, 2004.
21. P. Marayong, M. Li, A. M. Okamura, and G. D. Hager, "Spatial motion constraints: theory and demonstrations for robot guidance using virtual fixtures," in *IEEE ICRA*, 2003, vol. 2, pp. 1954-1959.
22. M. Li, M. Ishii, and R. H. Taylor, "Spatial motion constraints using virtual fixtures generated by anatomy," *IEEE Transactions on Robotics*, vol. 23, no. 1, pp. 4-19, 2007.
23. A. Kapoor and R. Taylor, "Constrained control for surgical assistant robots," in *IEEE ICRA*, 2006, pp. 231-236.
24. A. Menciassi, A. Eisinberg, G. Scalari, C. Anticoli, M. Carrozza, and P. Dario, "Force feedback-based microinstrument for measuring tissue properties and pulse in microsurgery," in *IEEE ICRA*, 2001, pp. 626-631.
25. U. Seibold, B. Kubler, and G. Hirzinger, "Prototype of Instrument for Minimally Invasive Surgery with 6-Axis Force Sensing Capability," in *IEEE ICRA*, 2005, pp. 496-501.
26. J. Peirs, J. Clijnen, D. Reynaerts, H. Van Brussel, P. Herijgers, B. Corteville, and S. Boone, "A micro optical force sensor for force feedback during minimally invasive robotic surgery," *Sensors and Actuators A: Physical*, vol. 115, no. 2-3, pp. 447-455, 2004.
27. P. Puangmali, H. Liu, L. D. Seneviratne, P. Dasgupta, and K. Althoefer, "Miniature 3-Axis Distal Force Sensor for Minimally Invasive Surgical Palpation," *IEEE/ASME Transactions on Mechatronics*, vol. 17, no. 4, pp. 646-656, 2012.
28. P. Polygerinos, A. Ataollahi, T. Schaeffter, R. Razavi, L. D. Seneviratne, and K. Althoefer, "MRI-compatible intensity-modulated force sensor for cardiac catheterization procedures," *IEEE TBME*, vol. 58, no. 3, pp. 721-726, 2011.
29. P. Berkelman, L. Whitcomb, R. Taylor, and P. Jensen, "A miniature instrument tip force sensor for robot/human cooperative microsurgical manipulation with enhanced force feedback," in *MICCAI*, 2000, pp. 247-286.
30. I. Iordachita, Z. Sun, M. Balicki, J. U. Kang, S. J. Phee, J. Handa, P. Gehlbach, and R. Taylor, "A sub-millimetric, 0.25 mN resolution fully integrated fiber-optic force-sensing tool for retinal microsurgery," *IJCARS*, vol. 4, no. 4, pp. 383-390, 2009.
31. X. He, M. Balicki, J. U. Kang, P. Gehlbach, J. Handa, R. Taylor, and I. Iordachita, "Force sensing micro-forceps with integrated fiber Bragg grating for vitreoretinal surgery," in *SPIE Phontics West*, 2012, 8218-82180W, pp. 1-7.
32. X. Liu, I. Iordachita, X. He, R. Taylor, and J. U. Kang, "Miniature fiber-optic force sensor based on low-coherence Fabry-Perot interferometry for vitreoretinal microsurgery," *Biomedical Optics Express*, vol. 3, no. 5, pp. 1062-1076, 2012.
33. X. He, J. Handa, P. Gehlbach, R. Taylor, and I. Iordachita, "A Sub-Millimetric 3-DOF Force Sensing Instrument with Integrated Fiber Bragg Grating for Retinal Microsurgery," *IEEE TBME*, accepted, 2013.
34. N. Cutler, M. Balicki, M. Finkelstein, J. Wang, P. Gehlbach, J. McGready, I. Iordachita, R. Taylor, and J. T. Handa, "Auditory force feedback substitution improves surgical precision during simulated ophthalmic surgery," *IOVS*, vol. 54, no. 2, pp. 1316-1324, 2013.
35. M. Balicki, A. Uneri, I. Iordachita, J. Handa, P. Gehlbach, and R. Taylor, "Micro-force sensing in robot assisted membrane peeling for vitreoretinal surgery," in *MICCAI*, 2010, vol. 13, pp. 303-310.
36. X. He, M. Balicki, P. Gehlbach, J. Handa, R. Taylor, and I. lordachita, "A novel dual force sensing instrument with cooperative robotic assistant for vitreoretinal surgery," in *IEEE ICRA*, 2013, pp. 213-218.
37. R. Kumar, P. Berkelman, P. Gupta, A. Barnes, P. S. Jensen, L. L. Whitcomb, and R. H. Taylor, "Preliminary experiments in cooperative human/robot force control for robot assisted microsurgical manipulation," in *IEEE ICRA*, 2000, pp. 610-617.
38. R. M. Murray, Z. Li, and S. S. Sastry, *A Mathematical Introduction to Robotic Manipulation*, CRC Press, 1994.
39. A. Krupa, G. Morel, and M. de Mathelin, "Achieving high-precision laparoscopic manipulation through adaptive force control," *Advanced Robotics*, vol. 18, no. 9, pp. 905-926, 2004.

The embodiments illustrated and discussed in this specification are intended only to teach those skilled in the art the best way known to the inventors to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:
1. A multi-force sensing instrument, comprising:
a tool comprising a tool shaft having a distal end and a proximal end;

a strain sensor arranged at a first position along said tool shaft;

at least one of a second strain sensor or a torque-force sensor arranged at a second position along said tool shaft, said second position being more towards said proximal end of said tool shaft than said first position; and a signal processor configured to communicate with said strain sensor and said at least one of said second strain sensor or said torque-force sensor to receive detection signals therefrom, wherein said signal processor is configured to process said signals to determine a magnitude and position of a lateral component of a force applied to said tool shaft when said position of said applied force is between said first and second positions, and wherein said lateral component of said force is a component of said force that lies in a plane that is orthogonal to said tool shaft at said position at which said force is applied.

2. A multi-force sensing instrument according to claim 1, wherein said signal processor is further configured to process said signals to determine a magnitude and position of a distal force applied to said tool shaft when said position of said distal force is beyond said first position towards said distal end of said tool shaft.

3. A multi-force sensing instrument according to claim 1, wherein said at least one of said second strain sensor or said torque-force sensor is a pair of strain sensors displaced with respect to each other along a distal to proximal axial direction along said tool shaft.

4. A multi-force sensing instrument according to claim 3, wherein the first-mentioned strain sensor and said pair of strain sensors comprise an optical fiber comprising first, second and third Fiber Bragg Gratings written therein corresponding respectively to said first-mentioned strain sensor and said pair of strain sensors, said optical fiber extending substantially parallel to said tool shaft.

5. A multi-force sensing instrument according to claim 3, wherein the first-mentioned strain sensor and said pair of strain sensors comprise a plurality of optical fibers each comprising first, second and third Fiber Bragg Gratings written therein corresponding respectively to said first-mentioned strain sensor and said pair of strain sensors, said plurality of optical fibers extending substantially parallel to said tool shaft and substantially parallel to each other.

6. A multi-force sensing instrument according to claim 5, wherein said plurality of optical fibers are arranged substantially equally spaced around a circumference of said tool shaft.

7. A multi-force sensing instrument according to claim 6, wherein said plurality of optical fibers are three optical fibers oriented about 120° apart around a circumference of said tool shaft.

8. A multi-force sensing instrument according to claim 7, wherein at least one of said three optical fibers provides temperature compensation information to said signal processor to correct for temperature changes.

9. A multi-force sensing instrument according to claim 5, wherein said first, second and third Fiber Bragg Gratings written in said optical fiber each have a unique central reflection wavelength under relaxed, equal temperature conditions to allow wavelength division multiplexing within said optical fiber.

10. A multi-force sensing instrument according to claim 9, further comprising:

an optical transmitter optically coupled to said optical fiber; and an optical receiver optically coupled to said optical fiber, wherein said optical receiver is configured to detect wavelengths of reflected light from each of said first, second and third Fiber Bragg Gratings.

11. A multi-force sensing instrument according to claim 1, wherein said tool is a surgical tool.

12. A multi-force sensing instrument according to claim 11, wherein said surgical tool is a micro-surgery surgical tool.

13. A multi-force sensing instrument according to claim 1, further comprising a second pair of strain sensors arranged at a third position along said tool shaft, said third position being more towards said proximal end of said tool shaft than said second position, wherein said second pair of strain sensors are displaced with respect to each other along a distal to proximal axial direction along said tool shaft.

14. A multi-force sensing instrument according to claim 1, further comprising a plurality of pairs of strain sensors arranged at corresponding pluralities of positions along said tool shaft successively more towards said proximal end of said tool shaft than said second position, wherein each of said plurality of pairs of strain sensors are displaced with respect to each other along a distal to proximal axial direction along said tool shaft.

15. A robotic system, comprising:

a robot having a tool connector;

a multi-force sensing instrument attached to said tool connector of said robot; and a feedback system configured to communicate with said multi-force sensing instrument to provide at least one of feedback control of said robot or feedback information to a user of said robotic system, wherein said multi-force sensing instrument comprises:

a tool comprising a tool shaft having a distal end and a proximal end;

a strain sensor arranged at a first position along said tool shaft;

at least one of a second strain sensor or a torque-force sensor arranged at a second position along said tool shaft, said second position being more towards said proximal end of said tool shaft than said first position; and a signal processor configured to communicate with said strain sensor and said at least one of said second strain sensor or said torque-force sensor to receive detection signals therefrom, wherein said signal processor is configured to process said signals to determine a magnitude and position of a lateral component of a force applied to said tool shaft when said position of said applied force is between said first and second positions, and wherein said lateral component of said force is a component of said force that lies in a plane that is orthogonal to said tool shaft at said position at which said force is applied.

16. A robotic system according to claim 15, wherein said robot is a cooperative-control robot that performs automated functions in response to a user's actions while using said tool to at least one of modify, assist or prevent manual operations of said user's actions.

17. A robotic system according to claim 15, wherein said robot is a tele-operated robot.

18. A method of controlling a robotic system, comprising:

performing an action with a multi-force sensing instrument, said multi-force sensing instrument, comprising:

a tool comprising a tool shaft having a distal end and a proximal end, a strain sensor arranged at a first position along said tool shaft, at least one of a second strain sensor or a torque-force sensor arranged at a second position along said tool shaft, said second position being more towards said proximal end of said tool shaft than said first position, and a signal processor configured to communicate with said strain sensor and said at least one of said second strain sensor or said torque-force sensor to receive detection signals therefrom, wherein said signal processor is configured to process said signals to determine a magnitude and position of a lateral component of a force applied to said tool shaft when said position of said applied force is between said first and second positions, and wherein said lateral component of said force is a component of said force that lies in a plane that is orthogonal to said tool shaft at said position at which said force is applied; and providing control signals to a robot based on said magnitude and position of said lateral component of said force determined from said multi-force sensing instrument such that said robot performs an automatic action in response thereto.

* * * * *